(12) United States Patent
Davenport et al.

(10) Patent No.: US 9,322,029 B2
(45) Date of Patent: Apr. 26, 2016

(54) TRANSGENIC PLANTS WITH REDUCED NITRATE CONTENT

(75) Inventors: Susan Davenport, London (GB); Pascaline Le Lay, London (GB); Juan Pablo Sanchez Tamburrino, London (GB)

(73) Assignee: BRITISH AMERICAN TOBACCO (INVESTMENTS) LIMITED, London (GB)

( * ) Notice: Subject to any disclaimer, the term of this patent is extended or adjusted under 35 U.S.C. 154(b) by 272 days.

(21) Appl. No.: 13/825,463

(22) PCT Filed: Sep. 6, 2011

(86) PCT No.: PCT/GB2011/051666
§ 371 (c)(1),
(2), (4) Date: Apr. 9, 2013

(87) PCT Pub. No.: WO2012/038717
PCT Pub. Date: Mar. 29, 2012

(65) Prior Publication Data
US 2013/0206155 A1    Aug. 15, 2013

(30) Foreign Application Priority Data

Sep. 22, 2010   (GB) .................................. 1015875.6
May 31, 2011   (GB) .................................. 1109073.5

(51) Int. Cl.
C12N 15/82   (2006.01)
A24B 13/00   (2006.01)
C07K 14/415  (2006.01)

(52) U.S. Cl.
CPC ............ *C12N 15/8243* (2013.01); *A24B 13/00* (2013.01); *C07K 14/415* (2013.01); *C12N 15/8261* (2013.01)

(58) Field of Classification Search
None
See application file for complete search history.

(56) References Cited

U.S. PATENT DOCUMENTS

| 2008/0127365 A1* | 5/2008 | Sanz Molinero .... C07K 14/415 800/278 |
| 2009/0183270 A1 | 7/2009 | Adams et al. |
| 2010/0206317 A1* | 8/2010 | Albino et al. .................. 131/88 |

FOREIGN PATENT DOCUMENTS

| CN | 1560256 A | 1/2005 |
| CN | 101395275 A | 3/2009 |
| EP | 0116718 A1 | 8/1984 |
| EP | 0242246 A1 | 10/1987 |
| EP | 0270822 A1 | 6/1988 |
| EP | 0369637 A2 | 5/1990 |
| GB | 2197653 A | 5/1988 |
| WO | 02/10210 A2 | 2/2002 |
| WO | 2007/022195 A2 | 2/2007 |
| WO | 2009/022183 A1 | 2/2009 |
| WO | 2010/053867 A1 | 5/2010 |

OTHER PUBLICATIONS

Fraisier et al. 2000, The Plant Journal 23: 489-496.*
Orsel et al., 2002, Journal of Experimental Botany 53: 825-833.*
Fraisier et al., 2000, The Plant Journal 23: 489-496.*
Chopin et al., 2007, Plant Cell 19: 1590-1602.*
Kuluev et al., 2008, Russian Journal of Plant Physiology 55: 687-693.*
Stepanov et al., 2008, Nicotine Tob. Res. 10: 1773-1782.*
Arabidopsis thaliana high affinity nitrate transporter 2.7 (AtNRT2,7), GenBank Accession No. NM_121461.3, published Apr. 19, 2010.*
Guo et al., 2004, Proceedings of the National Academy of Sciences USA 101: 9205-9210.*
Keskin et al., 2004, Protein Science 13: 1043-1055.*
Thornton et al., 2000, Nature Structural Biology, structural genomic supplement, Nov. 2000: 991-994.*
Zhang, et al., 1991, Plant Cell, 3, 1155-65.
Cornejo, et al., 1993, Plant Molecular Biology, 23, 567-581.
Hull, et al., 1986, EMBO J., 5, 3083-3090.
Helliwell and Gray, 1995, Plant Molecular Biology, 29 (3), 621-626.
Orsel, et al., Plant Physiology, 2002, 129, 886-896.
Bevan, M., 1984, Nucleic Acids Research, 12:8711-21.
Van Engelen, et al., 1995, Transgenic Research, 4:288-290.
Horsch, et al., 1985, Science, 227:1229-1231.
Thompson, et al., 1994, Nucleic Acids Research, 22, 4673-4680.
Thompson, et al., 1997, Nucleic Acids Research, 24, 4876-4882.
Masclaux, et al., 2000, Planta, 211, 510-518.
Cataldo, D.A., 1975, Community Soil Science and Plant Analysis, 6(1), 71-80.
Staaf, et al., 2005, Contributions to Tobacco Research, 21:321-330.

(Continued)

*Primary Examiner* — David T Fox
*Assistant Examiner* — Bratislav Stankovic
(74) *Attorney, Agent, or Firm* — McKee, Voorhees & Sease, PLC.

(57) ABSTRACT

The present invention relates to genetic constructs, which can be used in the preparation of transgenic plants. The constructs can have the ability of reducing nitrate concentration in the plant, in particular the plant's leaves, and for inducing a senescence-like phenotype. The invention extends to plant cells transformed with such constructs, and to the transgenic plants themselves. The invention also relates to methods of producing transgenic plants, and to methods of reducing nitrate content in plants. The invention also relates to harvested plant leaves, for example tobacco leaves, that have been transformed with the genetic constructs, and to various tobacco articles, such as smoking articles, comprising such harvested plant leaves.

5 Claims, 16 Drawing Sheets

(56) References Cited

OTHER PUBLICATIONS

De Roton, et al., 2005, Contributions to Tobacco Research, 21:305-320.

Fraisier, Vincent et al., "Constitutive expression of a putative high-affinity nitrate transporter in Nicotiana plumbaginifolia: Evidence for post-transcriptional regulation by a reduced nitrogen source", The Plant Journal, Blackwell Scientific Publications, Oxford, GB, vol. 23, No. 4, pp. 489-496, Aug. 1, 2000.

Good, Allen G. et al., "Can less yield more? Is reducing nutrient input into the environment compatible with maintaining crop production?", TRENDS in Plant Science, Elsevier Science, Oxford, GB, vol. 9, No. 12, pp. 597-605, Dec. 1, 2004.

Miller, Anthony J., et al., "Nitrate transport and signalling", Journal of Experimental Botany, vol. 58, No. 9, pp. 2297-2306, 2007.

Chopin, Franck, et al., "The Arabidopsis ATNRT2.7 Nitrate Transporter Controls Nitrate Content in Seeds", The Plant Cell, American Society of Plant Biologists, US, vol. 19, No. 5, pp. 1590-1602, May 1, 2007.

Shu-Chun, Fan et al., "The Arabidopsis Nitrate Transporter NRT1.7, Expressed in Phloem, Is Responsible for Source-to-Sink Remobilization of Nitrate", Plant Cell, vol. 21, No. 9, pp. 2750-2761, Sep. 2009.

International Search Report and Written Opinion, mailed Nov. 29, 2011, for International Application No. PCT/GB2011/051666, filed Sep. 6, 2011.

Written Opinion, mailed Sep. 10, 2012, for International Application No. PCT/GB2011/051666, filed Sep. 6, 2011.

International Preliminary Report on Patentability, issued Dec. 11, 2012, for International Application No. PCT/GB2011/051666, filed Sep. 6, 2011.

European Office Action in Application 11 755 425.3-1410. Ref. P103521EP. Sent May 22, 2015.

* cited by examiner

Figure: 1
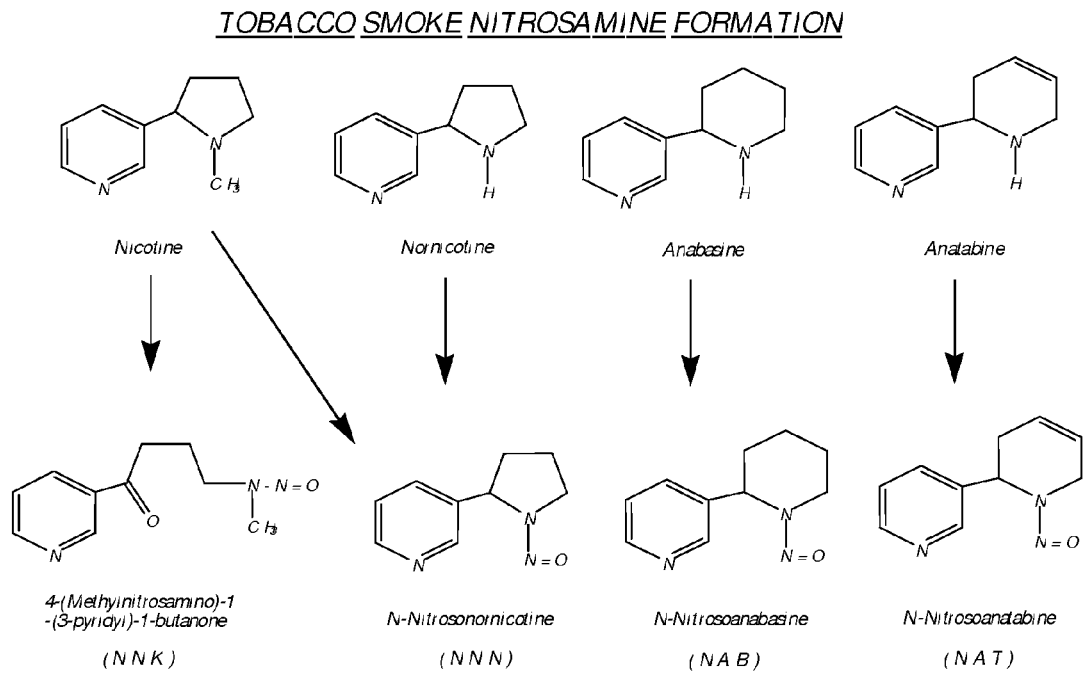
Figure: 2
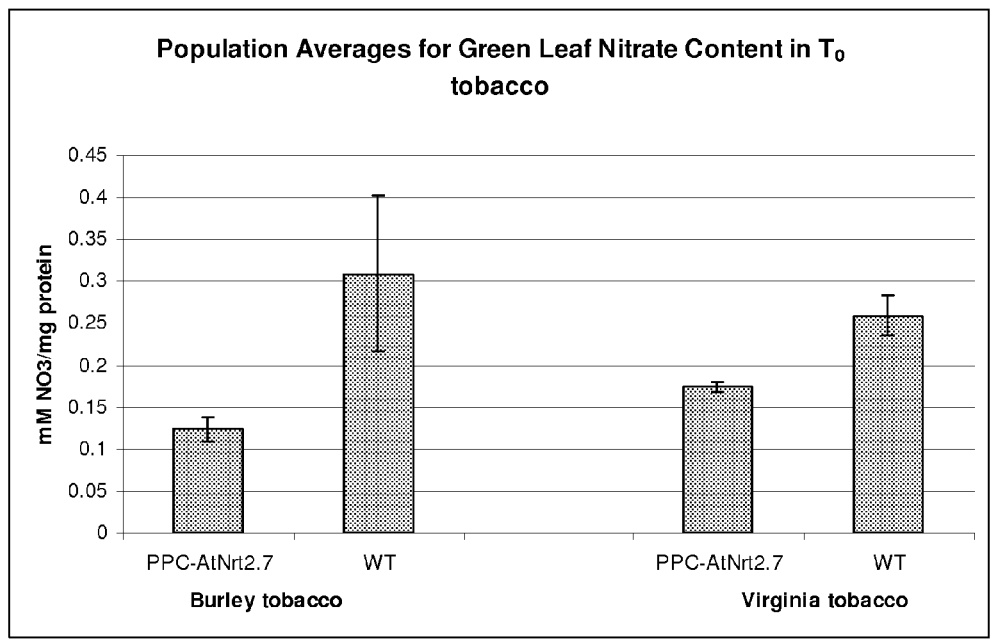

Figure: 3
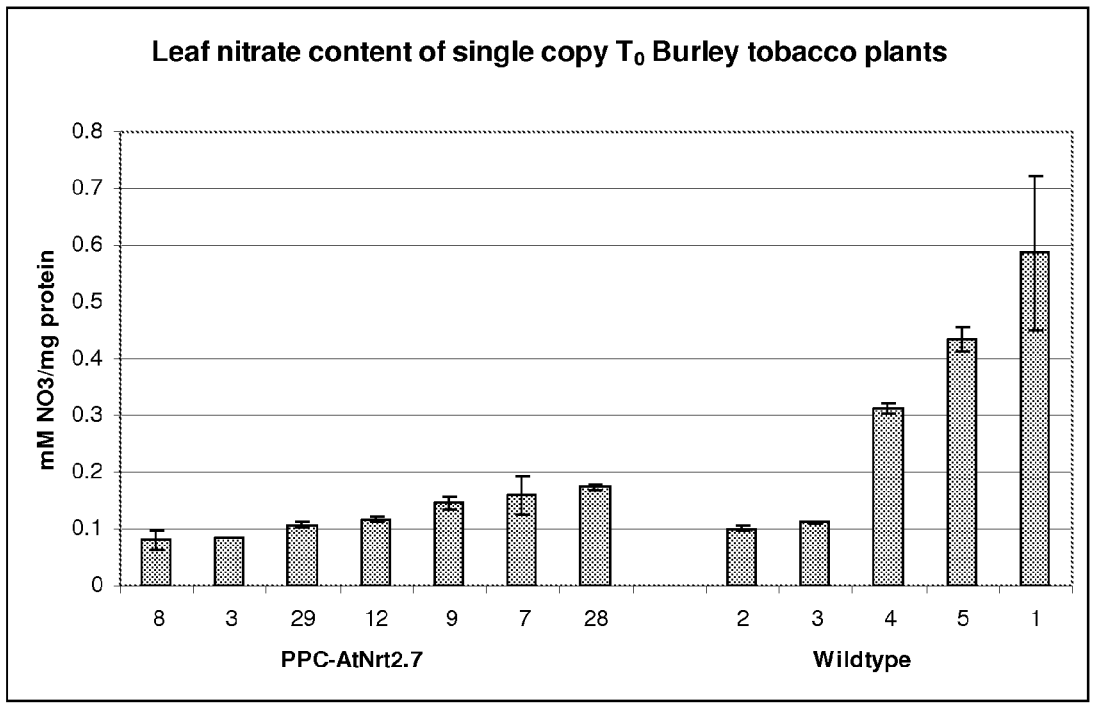
Figure: 4
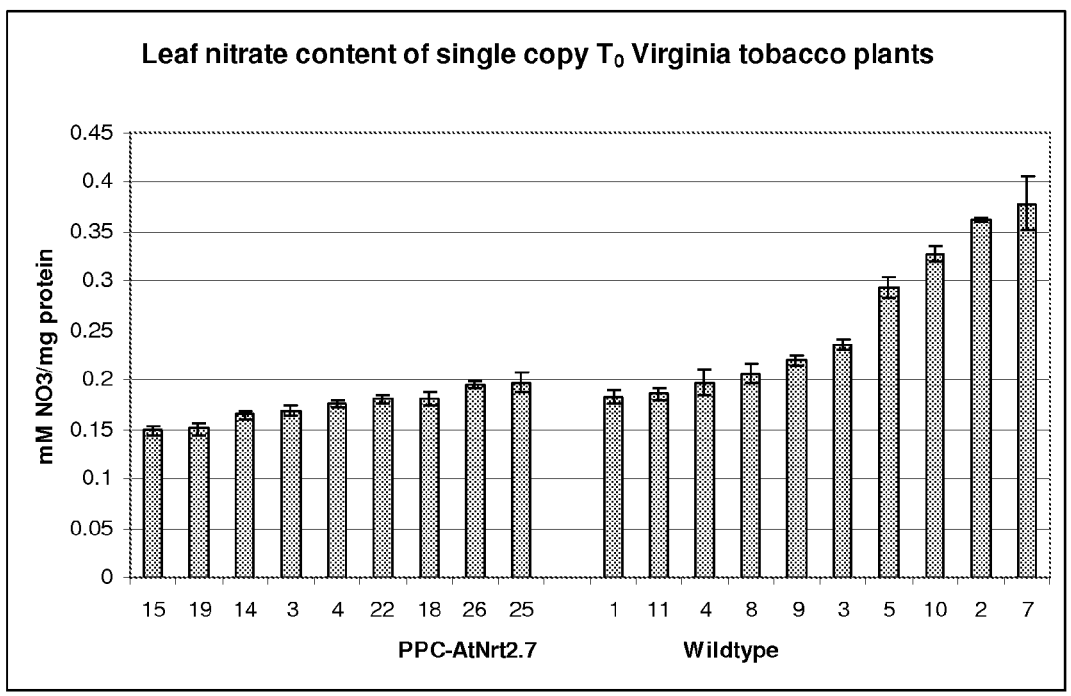

Figure: 5a
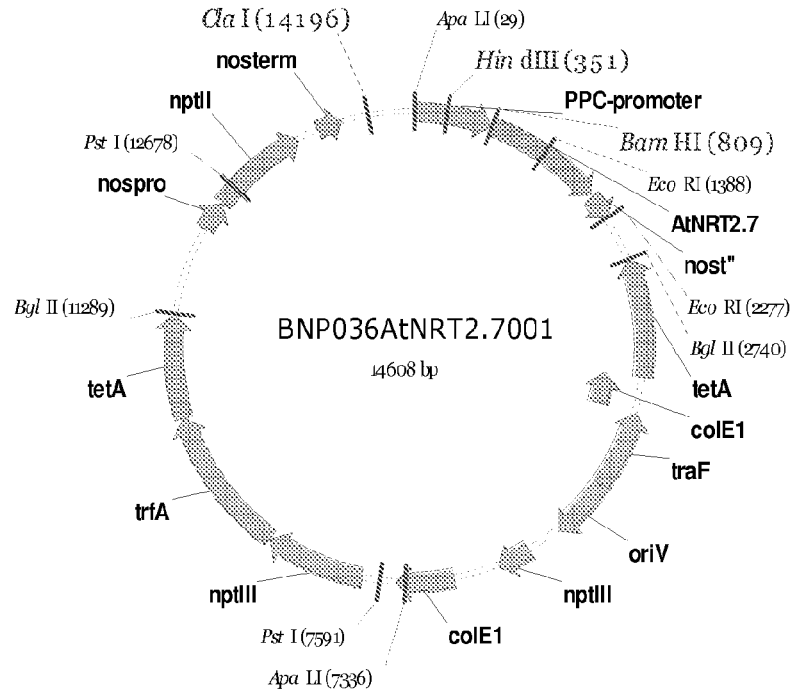
Figure: 5b
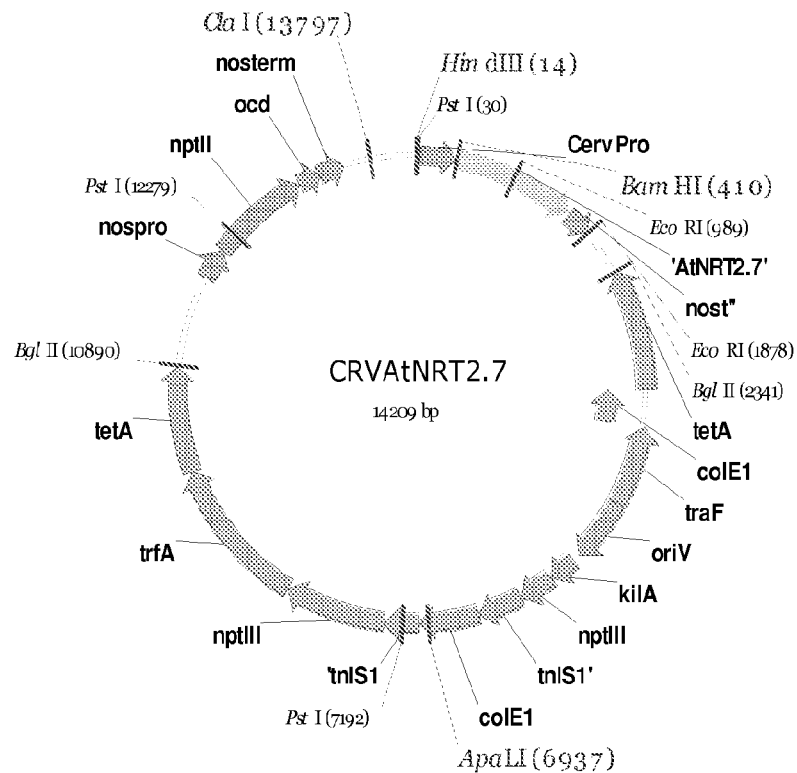

Figure: 6
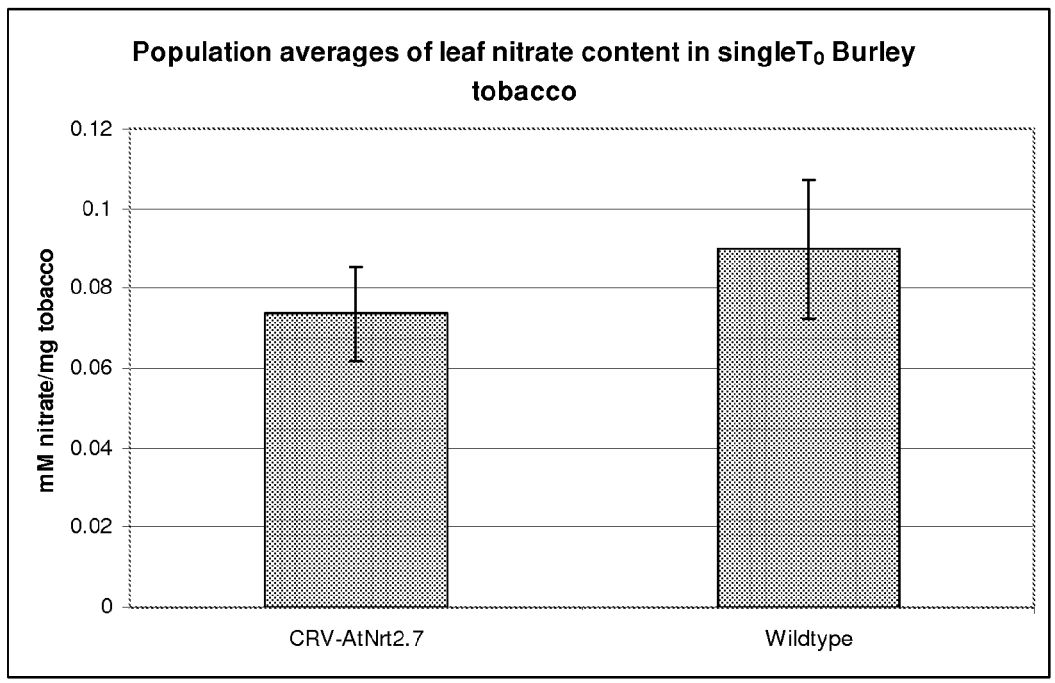
Figure: 7
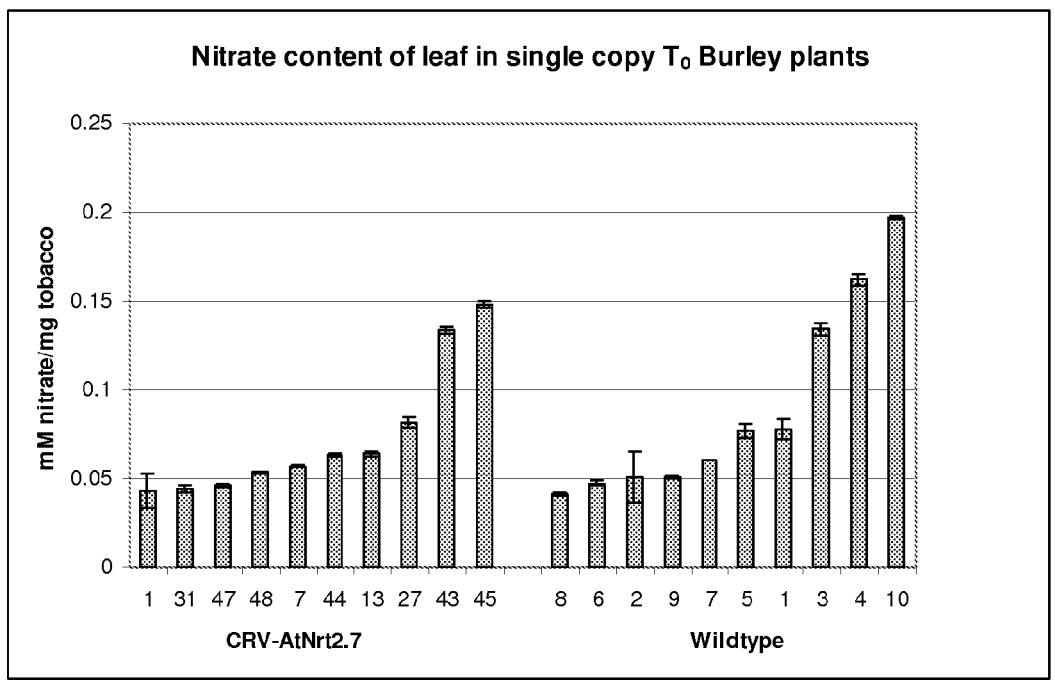

Figure: 8
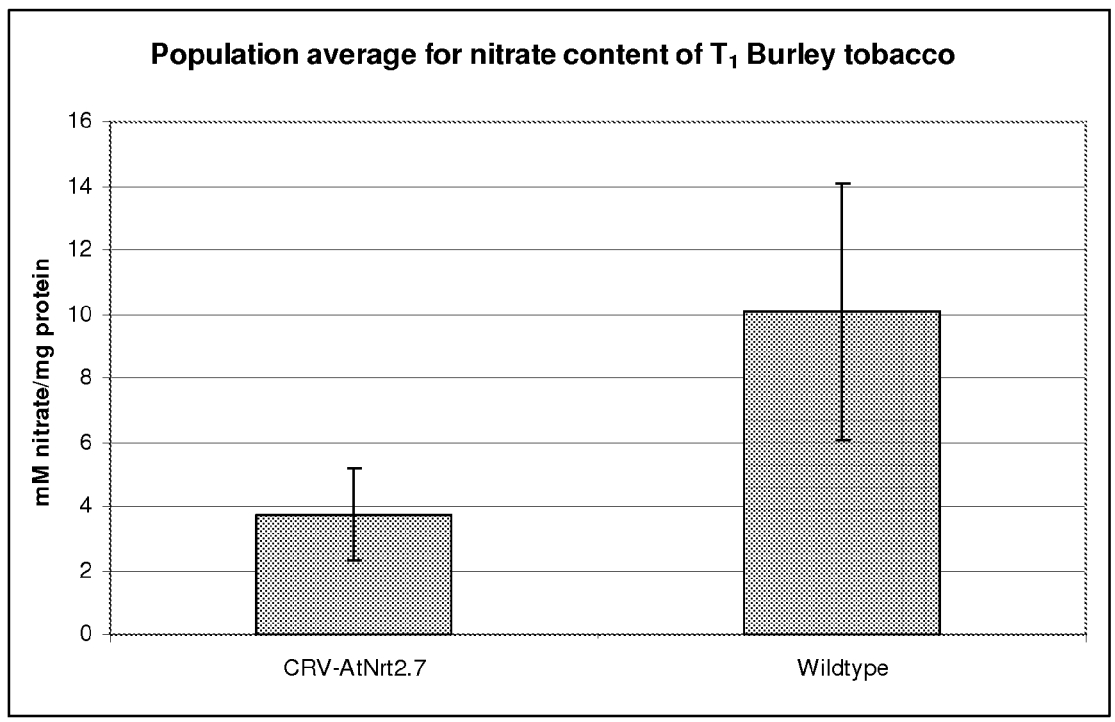
Figure: 9
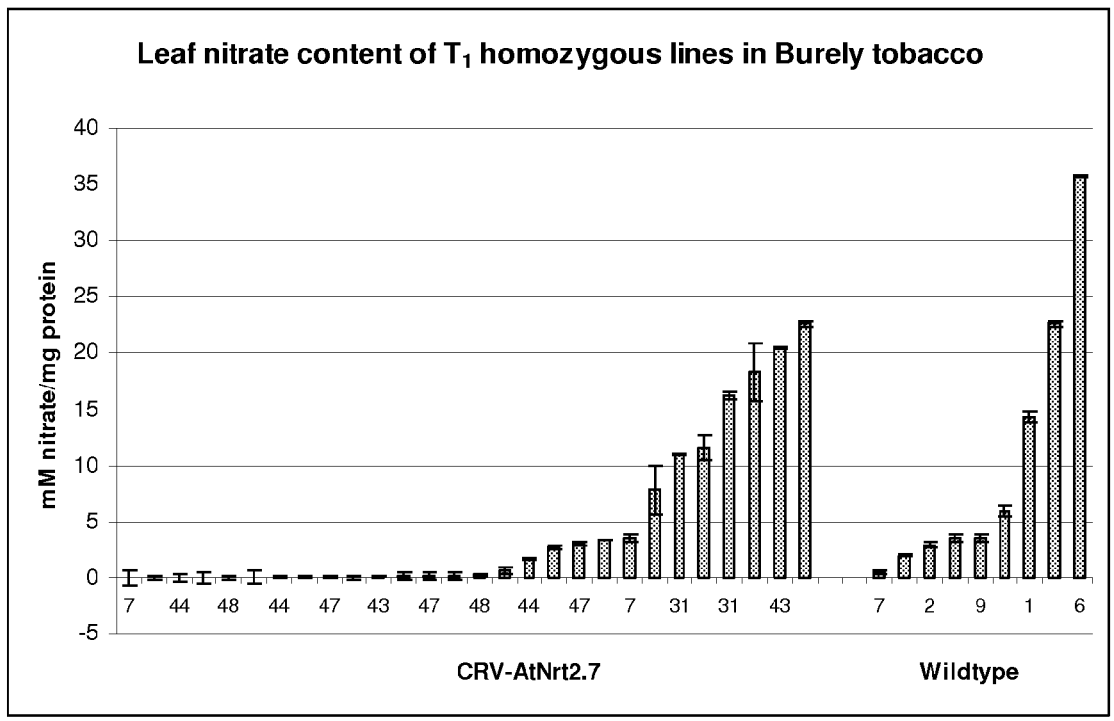

Figure: 10
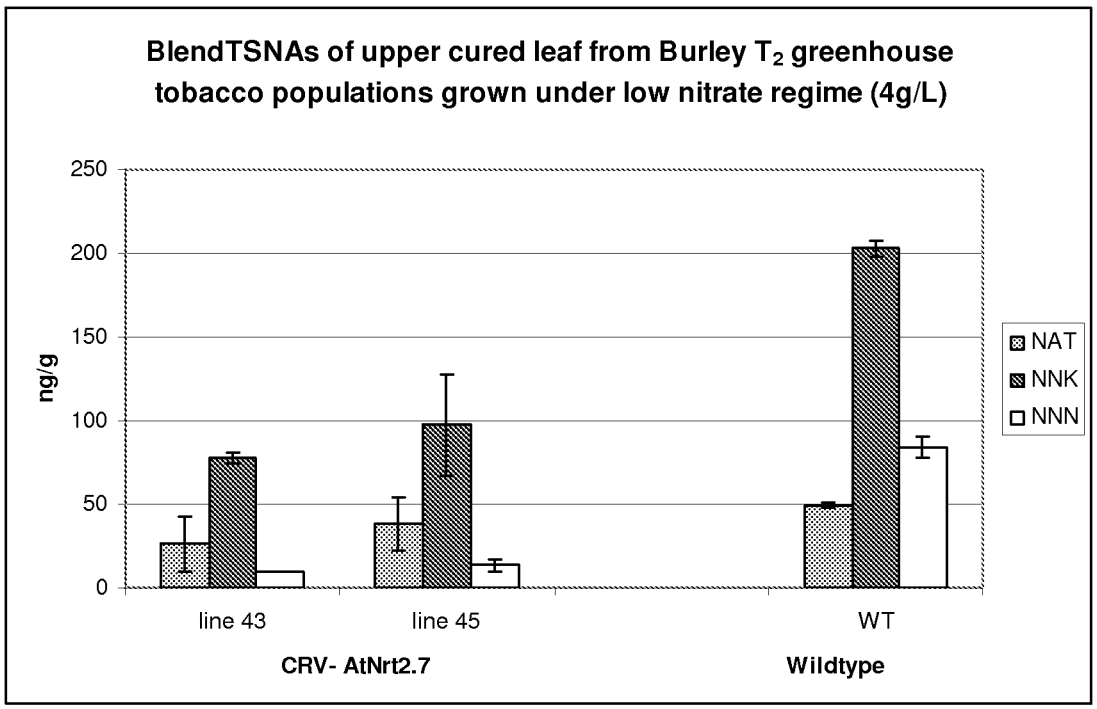
Figure: 11
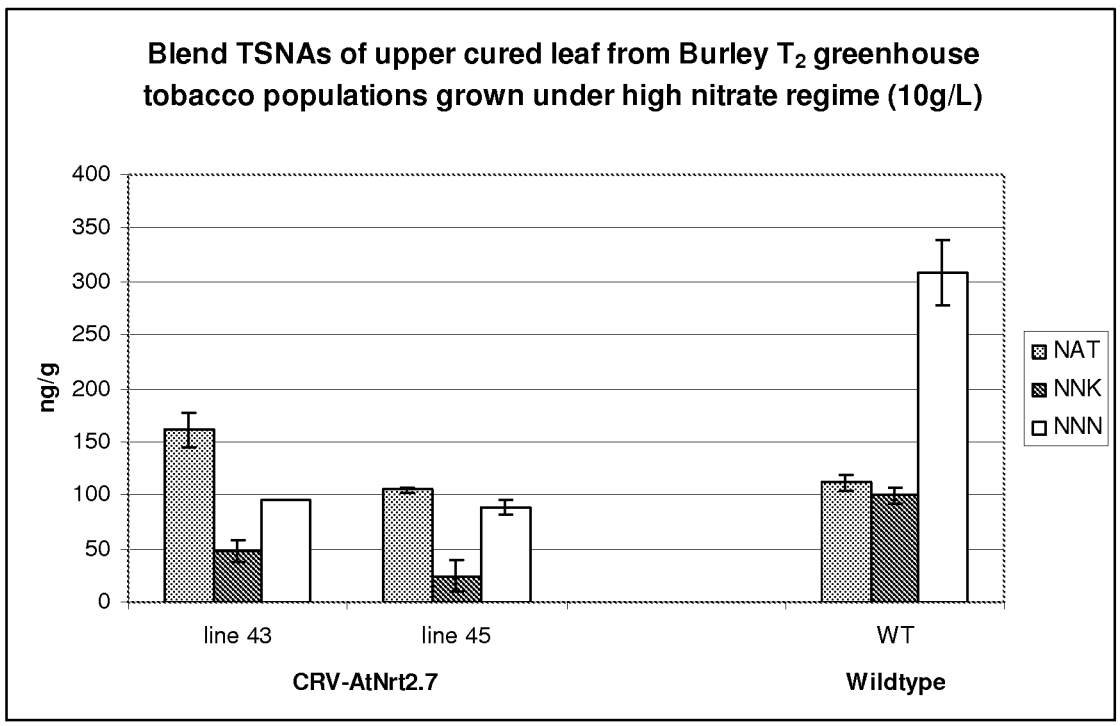

Figure: 12
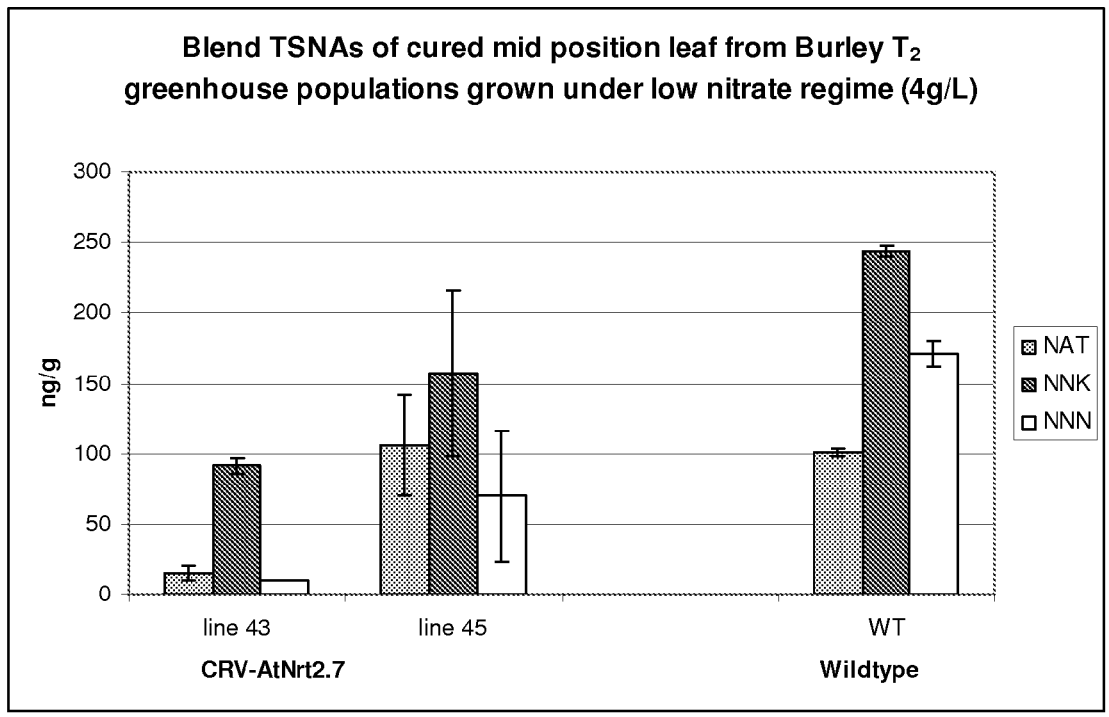
Figure: 13
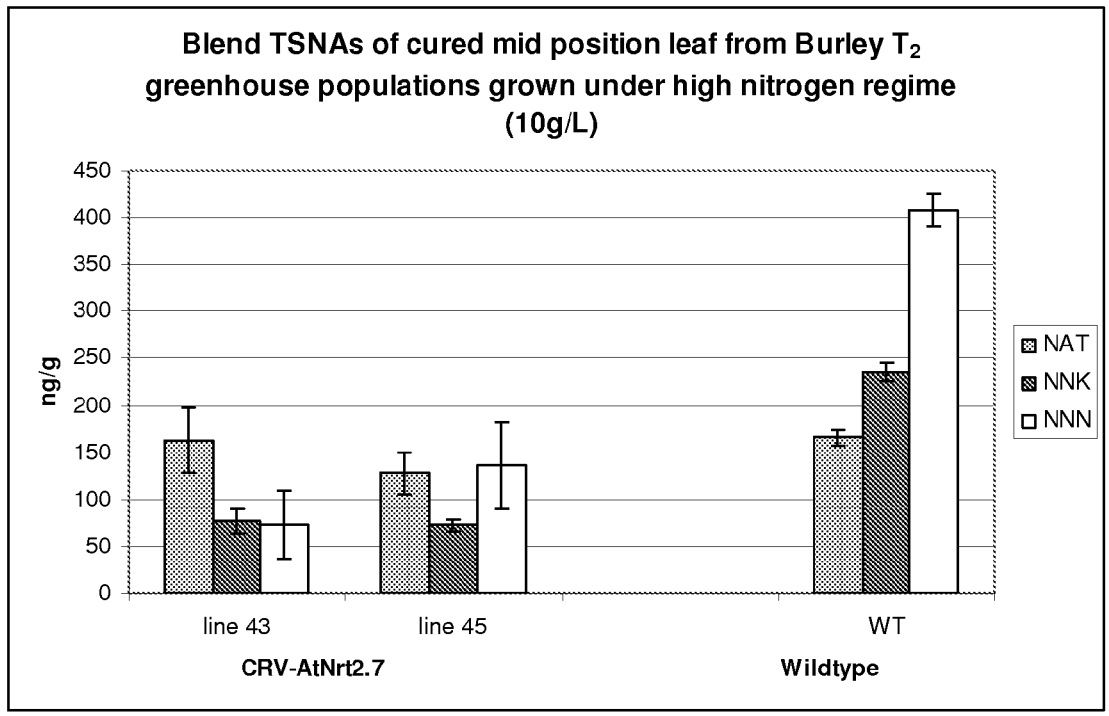

Figure: 14
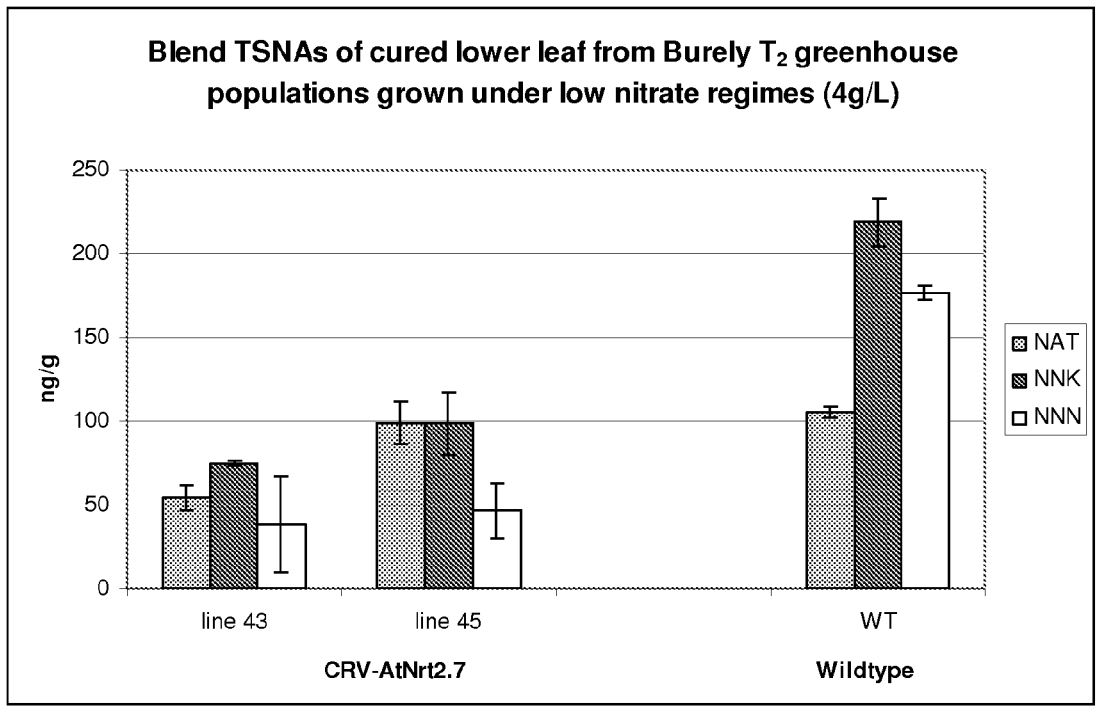
Figure: 15
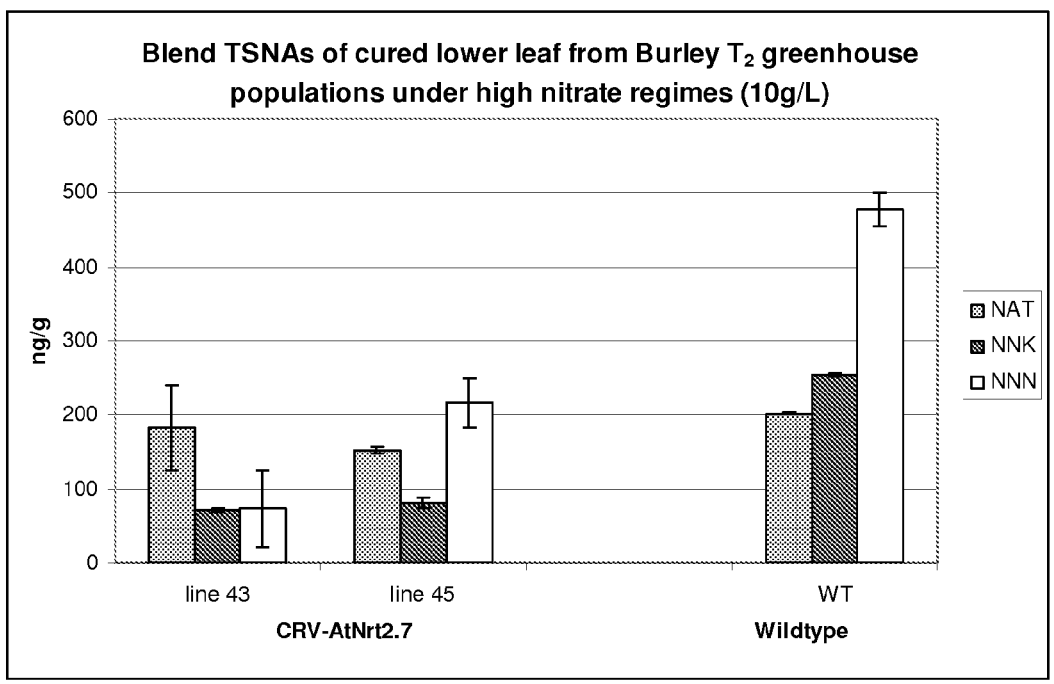

Figure: 16
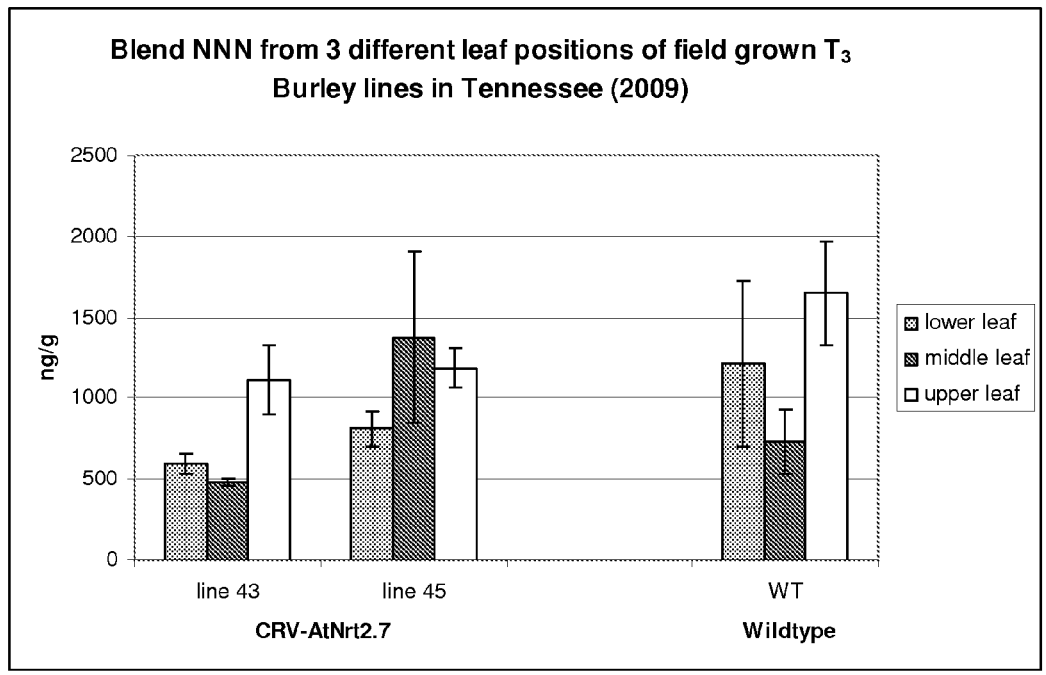
Figure: 17
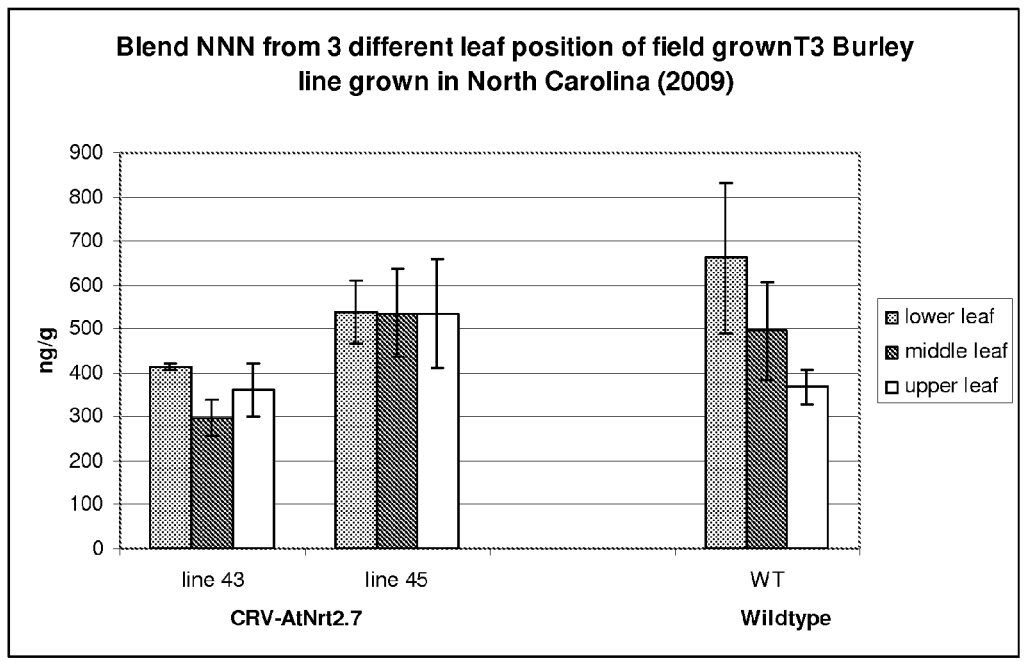

Figure: 18
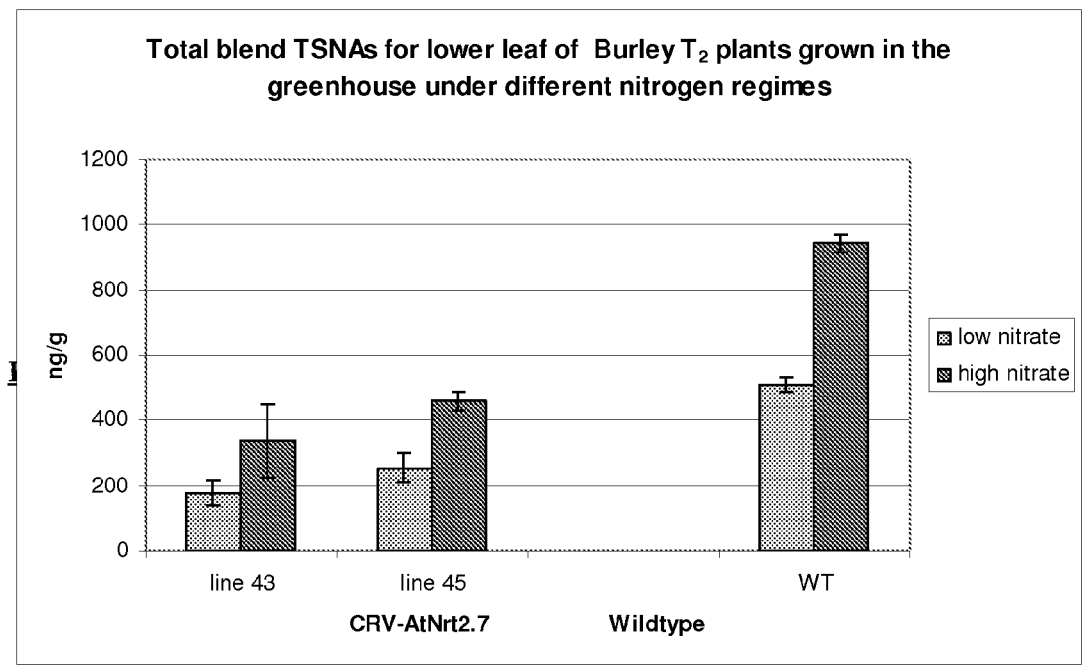
Figure: 19
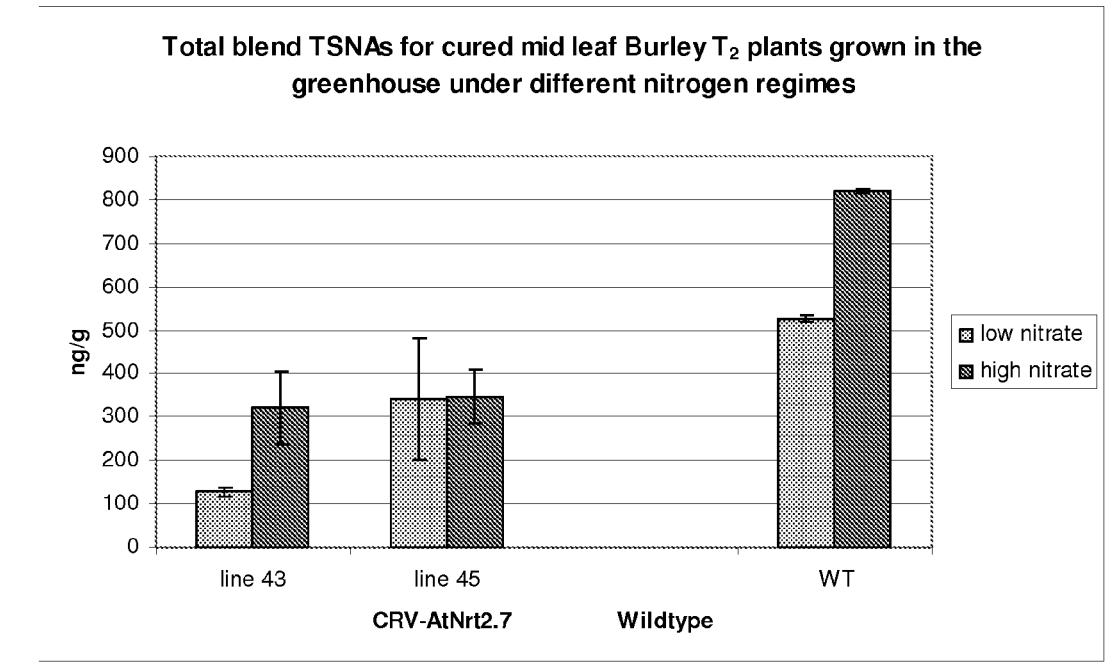

Figure: 20
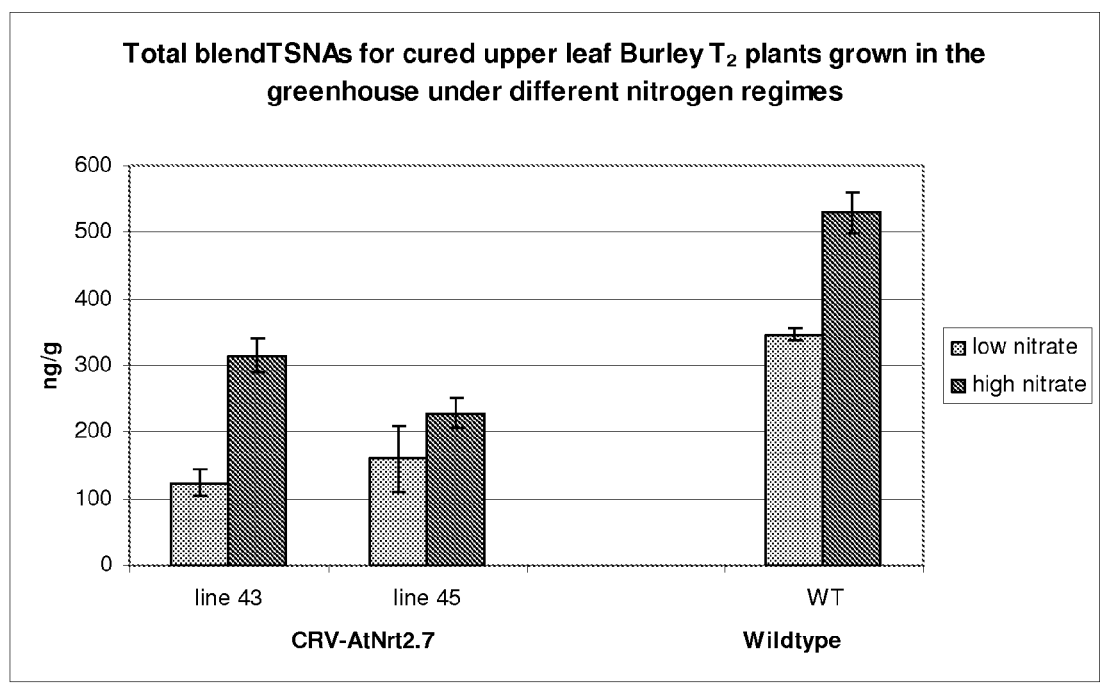

Figure: 21a
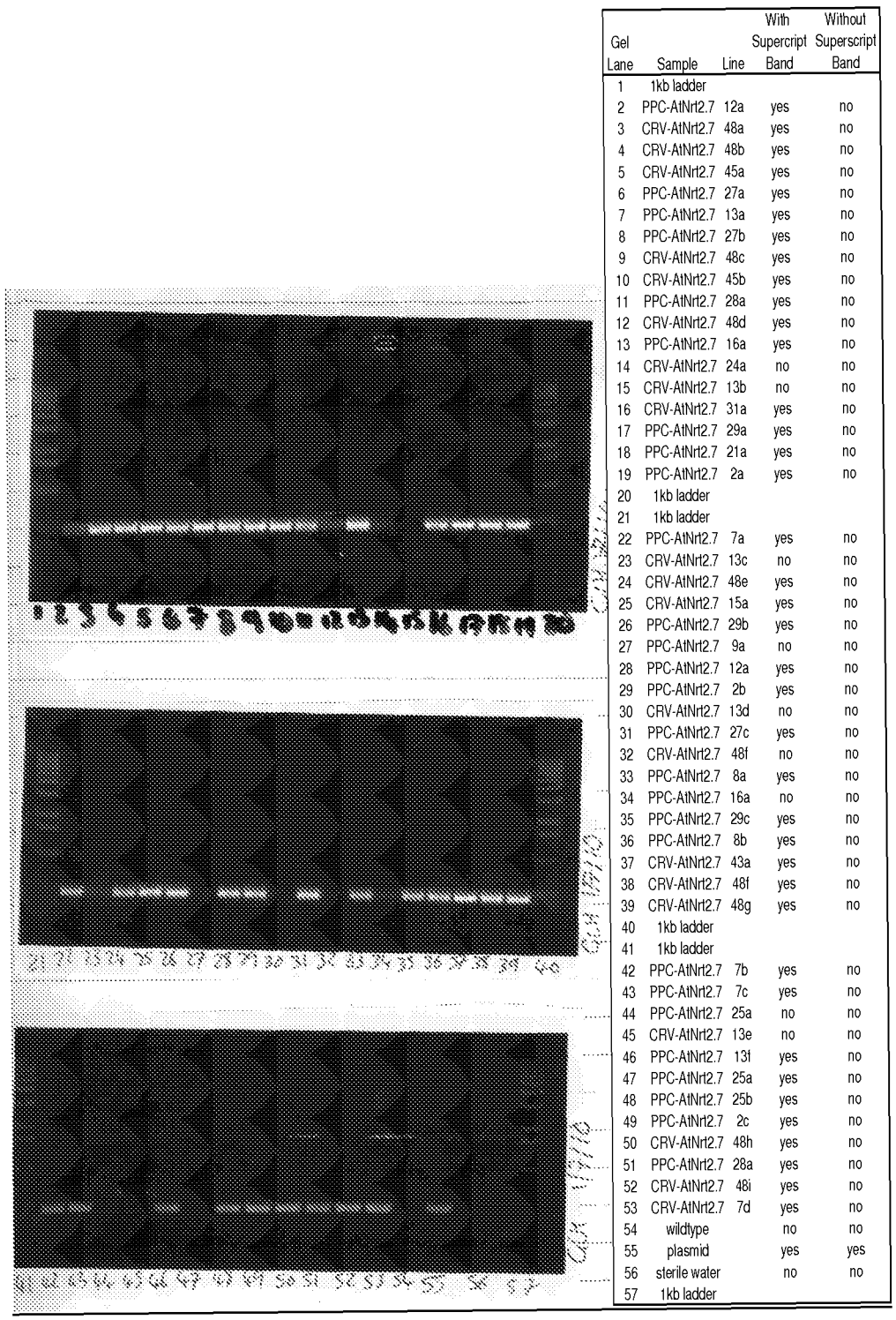

Figure: 21b
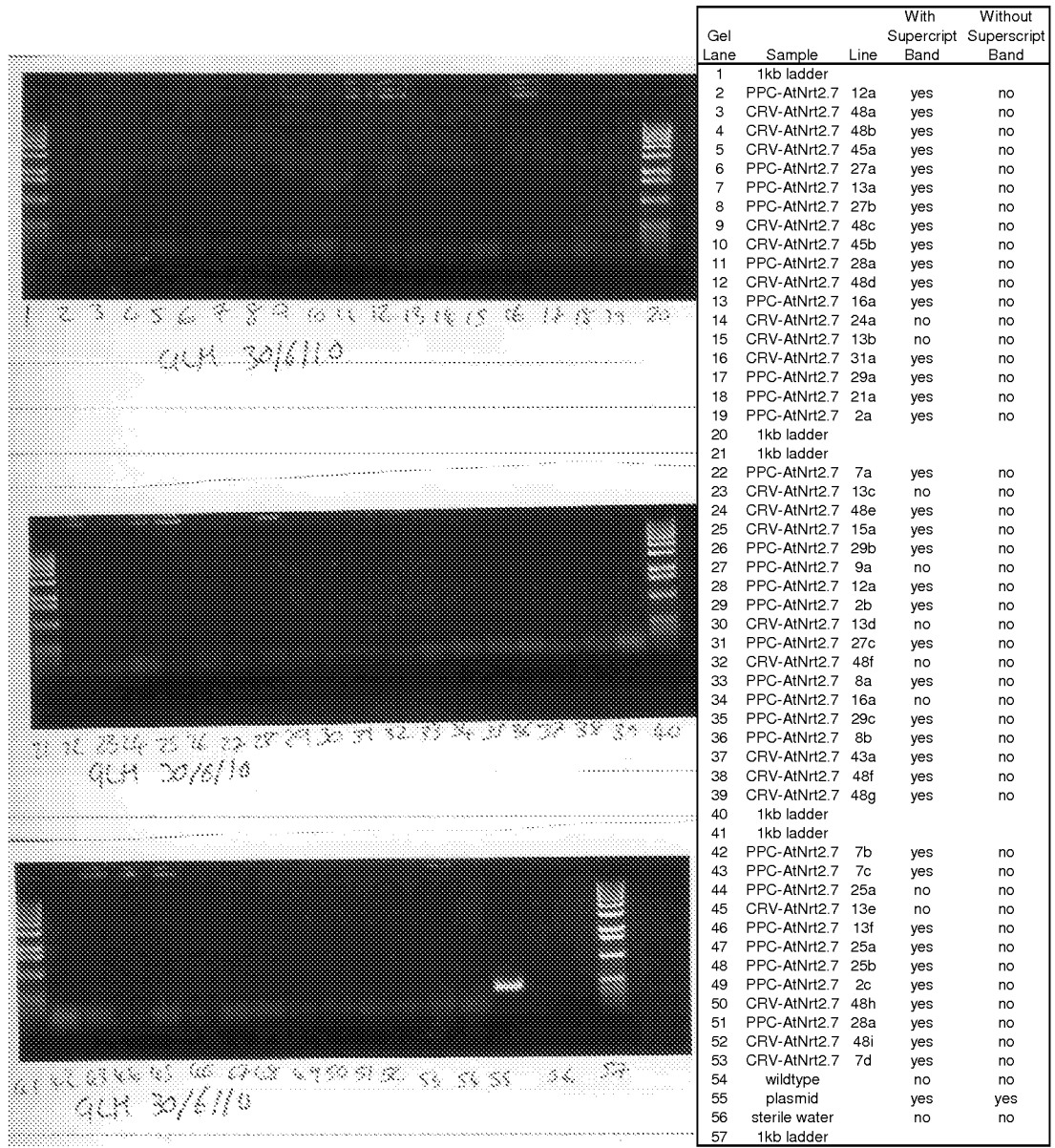

Figure: 22

```
                 1                                                50
35s   promoter   AGCTTGTCAACATGG-TGGAGCACGACACTCTCGTCTACTCCAAGAATAT
CERV  promoter   AGCTTG----CATGCCTGCAGGTCGAGCTTTTAGGATTCCATAGTGATAA
                 51                                               100
35s   promoter   CA-AAGATACAGTCT---CAGAAGACCA---GAGGGCTATTGAGACT--T
CERV  promoter   GATATGTTCTTATCTAAACAAAAAGCAAGCGTCGGCAAACCATACAGCT
                 101                                              150
35s   promoter   TTCAACAAGGGTAATATCGGGAAACCTCCTGGATTCCATTGCCAGCT
CERV  promoter   GTCCACAAAAAGGAAAGGCTGTAATAACAAGCGCACCCAGCTTCTCAG-T
                 151                                              200
35s   promoter   ATCTGTCACTTCATCGAAAGGACAGTAGAAAAGGAAGATGGCTTCTACAA
CERV  promoter   GGAAGATACTTTATCA----GACACTGAATAATG--GATGGACCCTACCA
                 201                                              250
35s   promoter   ATGCCATCATTGCGATAAAGCAAAGGCTATCGTTCA---AGATGCCTCTAC
CERV  promoter   ---CGATTAAACAGG--AGCCTCTGTCTAAAGTAAAGTAGATGCGTCTTT
```

Figure: 23

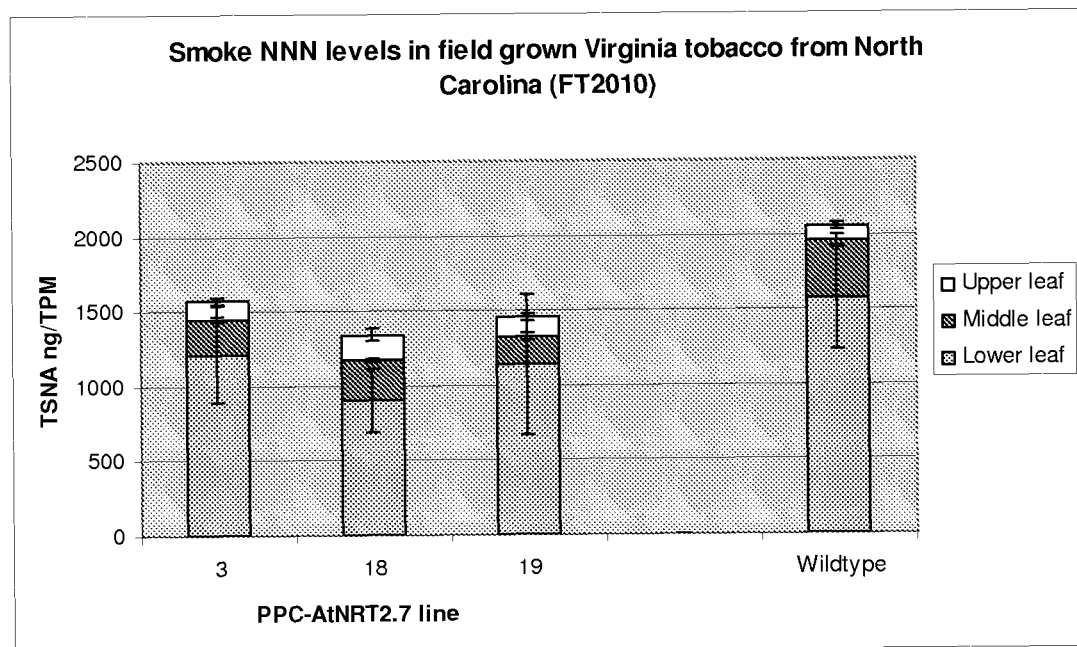

Figure: 24
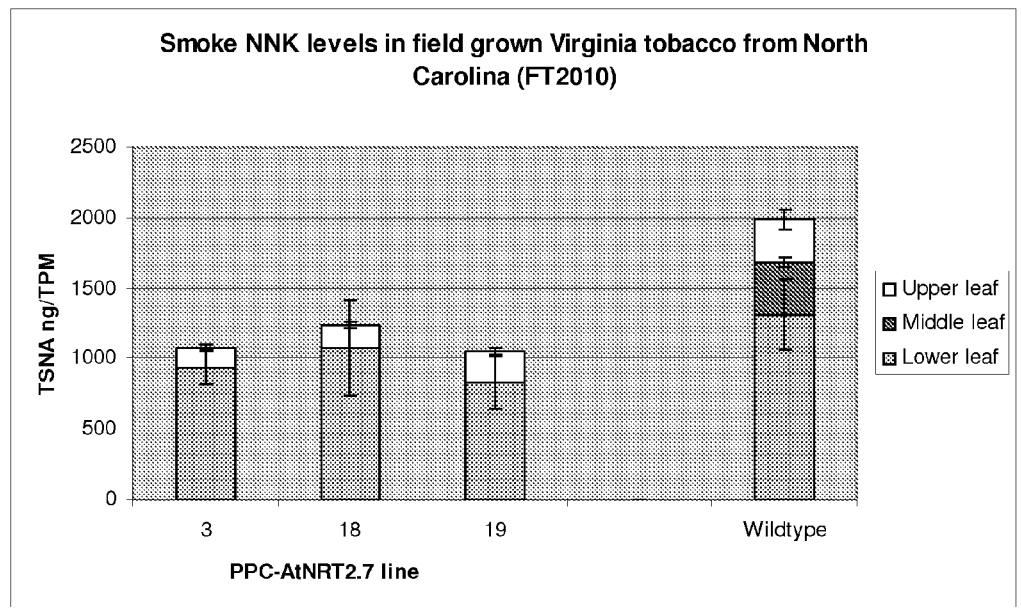
Figure: 25
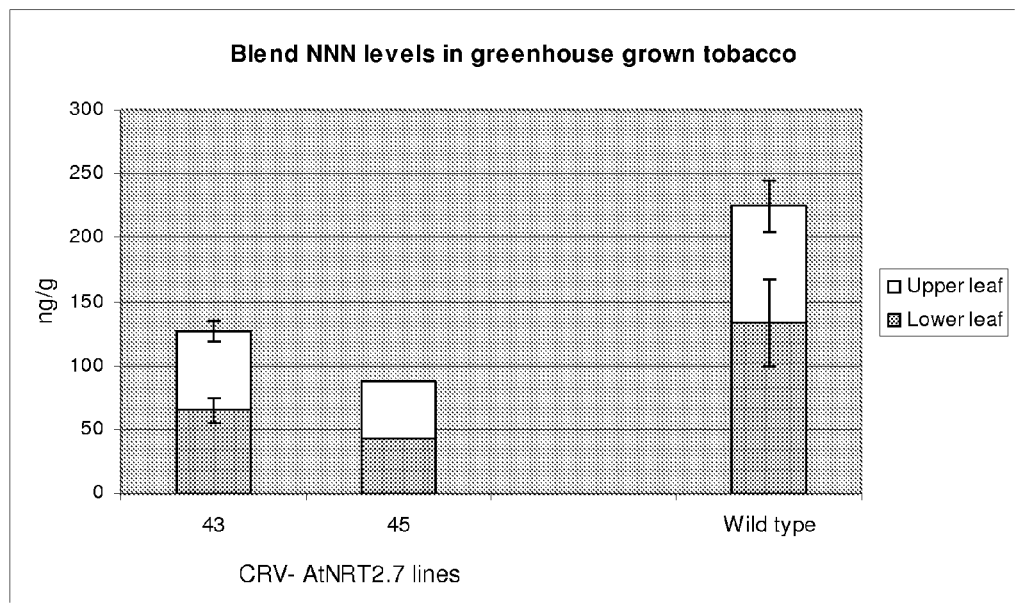

Figure: 26
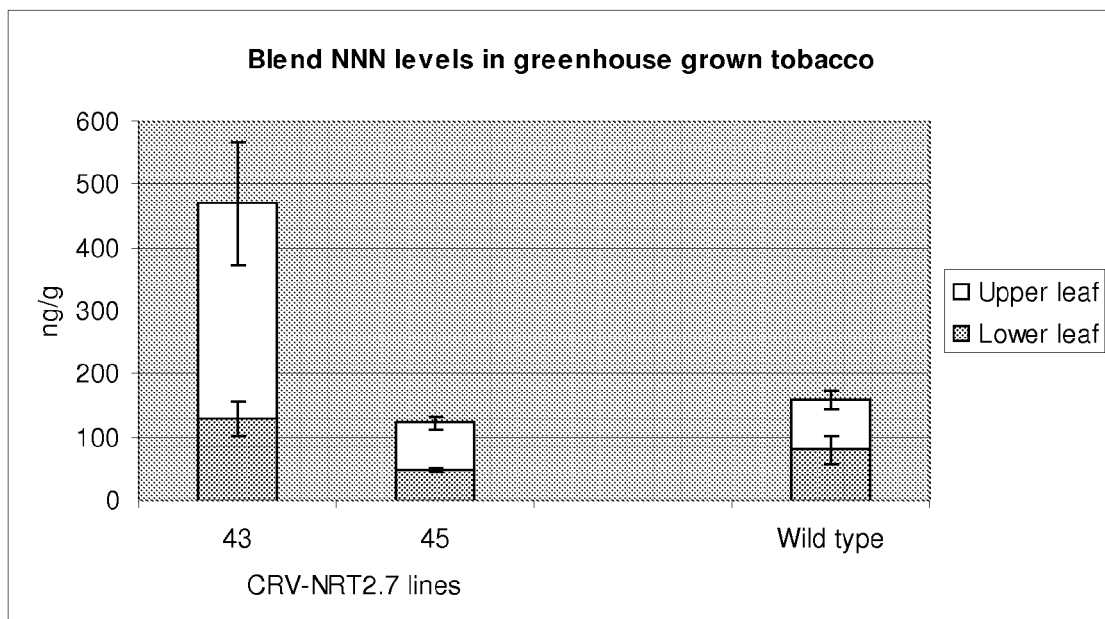

TRANSGENIC PLANTS WITH REDUCED NITRATE CONTENT

CLAIM FOR PRIORITY

This application is a National Stage Entry entitled to and hereby claims priority under 35 U.S.C. §§365 and 371 to corresponding PCT Application No. PCT/GB2011/051666, filed Sep. 6, 2011, which in turn claims priority to GB Application No. 1109073.5, filed May 31, 2011, and GB Application No. 1015875.6, filed Sep. 22, 2010. The entire contents of the aforementioned applications are herein expressly incorporated by reference.

STATEMENT REGARDING SEQUENCE LISTING

This application hereby incorporates by reference the sequence listing in the text file named BTMK 174 ooUS ST25.txt filed herewith having a size of 12 KB. The file was created on Jul. 15, 2013 and is submitted electronically via EFS-Web.

The present invention relates to genetic constructs, which can be used in the preparation of transgenic plants. The constructs can have the ability of reducing nitrate concentration in the plant, in particular the plant's leaves, and for inducing a senescence-like phenotype. The invention extends to plant cells transformed with such constructs, and to the transgenic plants themselves. The invention also relates to methods of producing transgenic plants, and to methods of reducing nitrate content in plants. The invention also relates to harvested plant leaves, for example tobacco leaves, that have been transformed with the genetic constructs, and to various tobacco articles, such as smoking articles, comprising such harvested plant leaves.

Nitrogen assimilation is of fundamental importance to the growth of plants. Of all the mineral nutrients required by plants, nitrogen is required in the greatest abundance. The main forms of nitrogen taken up by plants in the field are nitrate and ammonia, the principle components of nitrogenous fertilizers. Plants take up either nitrate or ammonium ions from the soil, depending on availability. Nitrate will be more abundant in well-oxygenated, non-acidic soils, whilst ammonium will predominate in acidic or water-logged soils. Experiments on growth parameters of tobacco clearly demonstrated that relative growth rate, chlorophyll content, leaf area and root area increased dramatically in response to increasing nitrate supply.

Roots take up nitrate and ammonia by the action of specific nitrate transporters (NTR). In plants, there are distinct transport systems that have different affinities for nitrate. The nitrate is then either reduced in the roots by the cytoplasmic enzyme nitrate reductase (NR) and enters the nitrogen assimilatory pathway, or it is transported to the shoots in the xylem. Nitrate is transported from the epidermal and cortical cells of the roots and into the vascular system to be transported to the shoots. It enters the leaves via the apoplast and is transported across the plasma membrane into the mesophyll cells. Here it is either stored in vacuoles, or reduced in the cytoplasm and enters the primary nitrogen assimilation pathway. When nitrate is present in excess, it is stored in the vacuole. This serves both as an osmoticum (i.e. supplements osmotic pressure), and as a source of mineral nitrogen to be used when nitrate uptake is minimal. The nitrate present in the cytoplasm is the starting point of primary nitrogen assimilation.

Nitrate is reduced in the cytosol by the cytoplasmic enzyme nitrate reductase (NR) to nitrite, which itself is rapidly reduced to ammonium by nitrite reductase (NiR) in the chloroplasts of leaves or in the plastids of non-photosynthetic organs. In the chloroplast, the ammonium then enters the glutamine synthetase/glutamate synthase cycle (GS/GOGAT), where it is incorporated into the amino acid pool.

The regulation of the activities of nitrate transporters, and nitrate and nitrite reductases is critical in controlling primary nitrogen assimilation throughout the plant, and has a significant impact on the growth and development of the plant. However, under certain conditions, nitrate may accumulate, mainly in green photosynthetically active tissues, where it is stored in the vacuoles of the mesophyll cells. High levels of nitrate accumulation can occur during periods of low temperature and/or solar irradiation (for example, in greenhouse crops during the winter), when there is less photosynthetic capacity to assimilate the stored nitrate, or as a result of high nitrate levels in the soil. An increase in nitrate levels can have a number of deleterious consequences, not only in terms of plant growth, but also in terms of human or animal health where the plant is consumed, as well as environmental consequences. Many of the adverse consequences of nitrate accumulation are mediated through the production of nitrite.

Therefore, to prevent nitrate accumulation, one strategy would be increasing nitrogen remobilisation in plants, for example when they become senescent, which could have important applications in crop production. Firstly, nitrogen remobilised from leaves can be transported to the younger leaves as well as the developing seed. Increasing the efficiency of nitrogen exit from senescent leaves could therefore potentially increase nitrogen supply to seeds and younger parts of the plant, and thereby increase crop yield and nitrogen use efficiency. This is clearly a valuable goal when the world population is increasing but crop yields are not increasing sufficiently to meet demand. One potential target crop is *Brassica napus* (oilseed rape), which has poor nitrogen efficiency due to poor nitrogen remobilisation from vegetative tissue. Another target crop is wheat, as the potential benefits of increasing grain protein content are great. Grain protein content not only affects nutritive value of wheat, but also determines grain usage and therefore market value. For example, increased grain protein content results in increased bread volume.

Also, an ability to increase nitrogen remobilisation could be very useful in the tobacco industry because it is known that residual nitrogen in tobacco leaves contributes to the formation of nitrosamines, as illustrated in FIG. 1. In particular, nitrate and nitrite act as precursors to tobacco-specific nitrosamine (TSNA) formation in cured leaf. Also, the formation of nitrosamines in the stomach is a result of endogenous nitrosation. Oral bacteria chemically reduce nitrate consumed in food and drink to nitrite, which can form nitrosating agents in the acidic environment of the stomach. These react with amines to produce nitrosamines and cause DNA strand breaks or cross linking of DNA. Another problem associated with an excess of nitrate is the formation of methaemoglobin which gives rise to blue baby syndrome, where the oxygen carrying capacity of haemoglobin is blocked by nitrite, causing chemical asphyxiation in infants.

As a consequence of these health concerns, a number of regulatory authorities have set limits on the amount of nitrate allowed in leafy green vegetables such as spinach and lettuce (e.g. European Commission Regulation 653/2003), depending on the time of harvest. These limits have resulted in any produce with a high nitrate content being unmarketable. Consequently, there have been efforts to reduce nitrate content of plants by managing the application of nitrogen-containing fertilisers or improved systems of crop husbandry. Some authorities have also set limits on the amounts of nitrate in drinking water.

There is therefore a need for means for alleviating the adverse effects associated with nitrate accumulation in plants. With this in mind, the inventors have developed a series of genetic constructs, which may be used in the preparation of transgenic plants, which exhibit surprisingly reduced nitrate concentrations.

Thus, according to a first aspect of the invention, there is provided a genetic construct comprising a promoter operably linked to a coding sequence encoding a polypeptide having nitrate transporter activity, with the proviso that the promoter is not a cauliflower mosaic virus 35S promoter.

As described in the Examples, the inventors have investigated the remobilisation of nitrogen in a plant, with a view to developing plants which exhibit decreased concentrations of nitrate, especially in the leaves. The inventors prepared a number of genetic constructs, in which a gene encoding a nitrate transporter protein was placed under the control of a promoter, which was not the CAMV 35S promoter, such as a constitutive promoter or a tissue-specific promoter. A variety of different tobacco species were then transformed with embodiments of these constructs, and the inventors observed, in nitrate transporter over-expressing lines grown in a greenhouse that, as the plant develops and starts flower initiation, possibly as the leaf switches from a sink to a source tissue, the main stem produces a brown/black colouration developed close to flowering time. The inventors have previously observed this phenotype in plants producing an excess of urea. Furthermore, they saw that lower leaves on the plant also began to develop chlorotic spots (i.e. pale patches due to insufficient chlorophyll), which were subsequently shown to have much lower nitrate content.

The inventors therefore measured the concentrations of tobacco-specific nitrosamines (TSNAs) in the transgenic plants, i.e. 4-(Methylnitrosamino)-1-(3-pyridyl)-1-butanone (NNK), N-Nitrosonornicotine (NNN) and N-Nitrosoanatabine (NAT), as shown in FIGS. 10-20, and were surprised to observe that over-expression of the nitrate transporter via the genetic construct resulted in a considerable decrease in the concentration of nitrate and hence TSNA concentrations in plant leaves. Previous studies with nitrate transporters have suggested that they cause an increase in nitrate uptake from the roots, which is then transported to plant vacuoles where it is stored. However, as a result of their experiments, the inventors have surprisingly found that constructs according to the invention, encoding a nitrate transporter, can cause the release of internal nitrate from the vacuoles, resulting in increased rates of nitrogen remobilisation away from the leaves, rather than towards the leaves, as previously thought. The inventors hypothesise that nitrogen may be being moved from leaves in the form of nitrate to the younger parts of the plant, such as the plant seeds and young shoots.

The promoter may be capable of inducing RNA polymerase to bind to, and start transcribing, the coding sequence encoding the polypeptide having nitrate transporter activity. The promoter in constructs of the invention may be a constitutive, non-constitutive, tissue-specific, developmentally-regulated or inducible/repressible promoter.

A constitutive promoter directs the expression of a gene throughout the various parts of the plant continuously during plant development, although the gene may not be expressed at the same level in all cell types. Examples of known constitutive promoters include those associated with the rice actin 1 gene (Zhang et al., 1991, Plant Cell, 3, 1155-65) and the maize ubiquitin 1 gene (Cornejo et al., 1993, Plant Molec. Biol., 23, 567-581). Constitutive promoters such as the Carnation Etched Ring Virus (CERV) promoter (Hull et al., 1986, EMBO J., 5, 3083-3090) are particularly preferred in the present invention.

A tissue-specific promoter is one which directs the expression of a gene in one (or a few) parts of a plant, usually throughout the life-time of those plant parts. The category of tissue-specific promoter commonly also includes promoters whose specificity is not absolute, i.e. they may also direct expression at a lower level in tissues other than the preferred tissue. Examples of tissue-specific promoters known in the art include those associated with the patatin gene expressed in potato tuber, and the high molecular weight glutenin gene expressed in wheat, barley or maize endosperm.

A developmentally-regulated promoter directs a change in the expression of a gene in one or more parts of a plant at a specific time during plant development, e.g. during senescence. The gene may be expressed in that plant part at other times at a different (usually lower) level, and may also be expressed in other plant parts.

An inducible promoter is capable of directing the expression of a gene in response to an inducer. In the absence of the inducer the gene will not be expressed. The inducer may act directly upon the promoter sequence, or may act by counteracting the effect of a repressor molecule. The inducer may be a chemical agent such as a metabolite, a protein, a growth regulator, or a toxic element, a physiological stress such as heat, wounding, or osmotic pressure, or an indirect consequence of the action of a pathogen or pest. A developmentally-regulated promoter can be described as a specific type of inducible promoter responding to an endogenous inducer produced by the plant or to an environmental stimulus at a particular point in the life cycle of the plant. Examples of known inducible promoters include those associated with wound response, temperature response, and chemically induced.

The promoter may be obtained from different sources including animals, plants, fungi, bacteria, and viruses, and different promoters may work with different efficiencies in different tissues. Promoters may also be constructed synthetically. Therefore, examples of suitable promoters include the Carnation Etch Ring Virus (CERV) promoter, the pea plastocyanin promoter, the rubisco promoter, the nopaline synthase promoter, the chlorophyll a/b binding promoter, the high molecular weight glutenin promoter, the α,β-gliadin promoter, the hordein promoter, the patatin promoter, or a senescence-specific promoter. For example, a suitable senescence-specific promoter may be one which is derived from a senescence-associated gene (SAG), and may be selected from a group consisting of SAG12, SAG13, SAG101, SAG21 and SAG18.

Preferably, the promoter is either the CERV promoter or the pea plastocyanin promoter.

Thus, according to a second aspect of the invention, there is provided a genetic construct comprising either a Carnation Etch Ring Virus (CERV) promoter or a pea plastocyanin promoter operably linked to a coding sequence encoding a polypeptide having nitrate transporter activity.

In one embodiment, the promoter may be a Carnation Etch Ring Virus (CERV) promoter, which will be known to the skilled technician, or a functional variant or a fragment thereof. (Hull et al., EMBO J., 5, 3083-3090). The DNA sequence encoding the CERV promoter is 232 bp long, and is referred to herein as SEQ ID No.1, as follows:

```
                        SEQ ID No. 1
AGCTTGCATGCCTGCAGGTCGAGCTTTTAGGATTCCATAGTGATAAGATA

TGTTCTTATCTAAACAAAAAAGCAGCGTCGGCAAACCATACAGCTGTCCA

CAAAAAGGAAAGGCTGTAATAACAAGCGGACCCAGCTTCTCAGTGGAAGA

TACTTTATCAGACACTGAATAATGGATGGACCCTACCACGATTAAAGAGG

AGCGTCTGTCTAAAGTAAAGTAGAGCGTCTTT
```

Therefore, the promoter in the construct of the invention may comprise a nucleotide sequence substantially as set out in SEQ ID No.1, or a functional variant or functional fragment thereof. The CERV promoter may be obtained from Cauliovirus or a plant species such as *Dianthus caryophyllus* (i.e. carnation) showing signs of the cauliovirus. In embodiments where the promoter is the CERV promoter, it will be appreciated that the promoter may comprise each of the bases 1-232 of SEQ ID No:1. However, functional variants or functional fragments of the promoter may also be used in genetic constructs of the invention.

A "functional variant or functional fragment of a promoter" can be a derivative or a portion of the promoter that is functionally sufficient to initiate expression of any coding region that is operably linked thereto. For example, in embodiments where the promoter is based on the CERV promoter, the skilled technician will appreciate that SEQ ID No:1 may be modified, or that only portions of the CERV promoter may be required, such that it would still initiate gene expression in the construct.

Functional variants and functional fragments of the promoter may be readily identified by assessing whether or not transcriptase will bind to a putative promoter region, and then lead to the transcription of the coding region into the polypeptide having nitrate transporter activity. Alternatively, such functional variants and fragments may be examined by conducting mutagenesis on the promoter, when associated with a coding region, and assessing whether or not gene expression may occur.

In another embodiment, the promoter may be a pea plastocyanin promoter, which will also be known to the skilled technician, or a functional variant or a fragment thereof. (Helliwell and Gray, 1995, Plant Mol. Biol. 29(3):621-626). The DNA sequence encoding the pea plastocyanin promoter is 783 bp long, and referred to herein as SEQ ID No.2, as follows:

```
                        SEQ ID No. 2
TATGCAACTTACAACGTGCACTCGCGGAGGATTGGACGTGTGCAACTTAC

AACGTACGCATTGTTCGTTCATACAATAGTGTAGAATTGGACATGTGCAA

CTTACAACATGTGCAACTTACAACGTGCGCTCGCGGAGGAATGTGAAGTT

GAACACGTACAACTTACGTCATTTGTGCATGCAGAAGCATAGAGCTGAGC

ACACAATTCATAATTTGAAGGACACATGATTTGCTATAAAGAACTCTTTA

GAAGTACCACAACTTTGACTGAGTTTGATATAGCTAATAAAGATGGAGCT

CATTATAATTTGAATGGCATAATCAAGCTAAACGAACAAGCTTAGTTAAT

CATGTTAAACAACAATTCTTTGTAATAATAAATTGTCTTTCAACTAGTCC

AAGTTTATGAGTTGATTCTTCGGAATAAATTAGAAAATATCTTAGATTTT

ATACTTCATTGATTATTTCATAGAGCAAGTAGGAGAAATAAAAATATACT

AGTATTATTTACTAAAAAAAATCTAAGCCACGTCGGAGGATAACATCCAA

CCCAGCCAATCACAGCAATGTTCATCAGATAACCCACTTTAAGCCCACGC

ACTCTGTGGCACATCTACATTATCTAAATCACATATTCTTCCACACATCT

TAGCCACACAAAAACCCAATCCACATCTTTATCATCCATTCTATAAAAAA

TCACCTTCTGTGTGTCTCTCTTTCGATTCCCTTCAAACACATACAAATTC

AGTAGAGAAGAAACTCATTACTCTTGAGAAAAA
```

Therefore, the promoter in the construct of the invention may comprise a nucleotide sequence substantially as set out in SEQ ID No.2, or a functional variant or functional fragment thereof. The pea plastocyanin promoter may be obtained from *Pisum* spp., such as *Pisum sativum* (i.e. pea).

The polypeptide having nitrate transporter activity in the construct of the first or second aspect may be derived from any suitable source, such as a plant. The coding sequence, which encodes the polypeptide having nitrate transporter activity, may be derived from a suitable plant source, for example from *Arabidopsis* spp., *Oryza* spp., *Populus* spp. or *Nicotiana* spp. The coding sequence may be derived from *Arabidopsis thaliana, Oryza sativa, Populus tremula* or *Nicotiana tabacum*.

The coding sequence in the construct may encode the *Arabidopsis* nitrate transporter, AtNRT 2.7 (as described in Orsel et al., Plant Physiology, 2002, 129, 886-896). AtNRT 2.7 genomic DNA contains one intron (78 nucleotides long) localised between exon 1 (298 nt long) and exon 2 (1184 nt long). The genomic DNA sequence (including introns and exons) encoding one embodiment of an *Arabidopsis* nitrate transporter is provided herein as SEQ ID No:3, as follows:

```
                                  SEQ ID No: 3
ATGGAGCCATCTCAACGCAACACCAAACCGCCGTCGTTTTCAGATTCCAC

TATCCCGGTTGATTCCGATGGTCGAGCCACCGTCTTCCGACCATTCTCTC

TCTCCTCGCCACACTCACGAGCCTTTCACCTAGCTTGGCTCTCACTCTTC

TCATGCTTCTTCTCCACCTTCTCCATCCCTCCTCTGGTCCCCGTCATCTC

CTCCGACCTCAACCTCTCTGCCTCCACCGTATCCGCCGCCGGAATCGCTT

CCTTCGCTGGCTCCATCTTCTCTCGCCTCGCTATGGGACCACTCTGTGAT

CTCATCGGACCACGTACTTCCTCAGCGATTCTCTCTTTTCTCACCGCTCC

TGTAATCCTCTCCGCCTCACTCGTCTCCTCTCCGACGTCCTTCATCCTCG

TCCGTTTCTTCGTCGGCTTCTCGCTCGCTAATTTCGTAGCCAATCAATAC

TGGATGTCCTCCATGTTCTCCGGTAACGTCATTGGTCTCGCTAACGGTGT

CTCAGCCGGTTGGGCTAACGTCGGCGCCGGTATCTCTCAGCTCCTTATGC

CTCTCATATACTCCACCATAGCCGAATTCCTTCCACGCGCCGTCGCCTGG

CGCGTGTCCTTCGTATTTCCCGCCATTTTTCAGGTTACAACGGCCGTCCT

CGTTCTCCTCTACGGCCAAGATACTCCCCACGGTAACAGAAAAAACTCGA

ACCAGAACAAACTCACAATTCCTGAAGAAGAAGAAGTACTAGTAGTTGAA

GAAGACGAACGTTCCAGTTTCGTCGAGATCCTAATCGGCGGACTTGGAAA

TTACAGAGCGTGGATCTTAGCGCTGCTCTACGGATACTCGTACGGCGTCG

AGCTAACGACGGACAACGTGATCGCCGGATATTTCTACGAGAGATTTGGA

GTGAATCTGGAGGCGGCGGGGACGATCGCGGCGAGTTTCGGGATATCGAA

CATTGCGTCGCGACCGGCGGGAGGGATGATATCGGATGCGCTGGGGAAGA
```

-continued
```
GATTCGGTATGAGAGGGAGGCTGTGGGGCTATGGATCGTGCAATCGGTG
GCTGGGTTGTTGTGCGTGTTACTCGGACGAGTCAACTCGCTCTGGGGATC
AATCCTCGTCATGTGGGTCTTCTCTGTTTTCGTTCAAGCTGCTTCTGGCC
TTGTATTTGGCGTGGTCCCTTTCGTCTCCACGCGGTTAGTTTAAAGTCTA
CCAATCCGGTTTTTGCTAATAATTTCGGTTTGGTTTTAATTTGGTTTTGT
TTATAATGACAGATCGTTAGGAGTGGTGGCGGGAATTACGGGAAGCGGCG
GTACGGTTGGTGCGGTGGTGACGCAGTTTCTGTTGTTTTCCGGTGATGAT
GTTCGAAAACAGAGAAGCATTTCACTTATGGGTTTGATGACTTTTGTGTT
TGCTCTTTCTGTTACATCAATTTACTTTCCACAATGGGTGGAATGTGTT
GTGGGCCTTCGTCATCTTCCGAAGAAGAAGATATTTCTCGGGGACTCCTT
GTAGAAGACGAAGATGAAGAAGGTAAAGTGGTTAGTGGTAGTCTACGTCC
CGTTTGTTGA
```

The cDNA sequence (exons only) encoding the *Arabidopsis* nitrate transporter is provided herein as SEQ ID No:4, as follows:

```
                                          SEQ ID No: 4
ATGGAGCCATCTCAACGCAACACCAAACCGCCGTCGTTTTCAGATTCCAC
TATCCCGGTTGATTCCGATGGTCGAGCCACCGTCTTCCGACCATTCTCTC
TCTCCTCGCCACACTCACGAGCCTTTCACCTAGCTTGGCTCTCACTCTTC
TCATGCTTCTTCTCCACCTTCTCCATCCCTCCTCTGGTCCCCGTCATCTC
CTCCGACCTCAACCTCTCTGCCTCCACCGTATCCGCCGCCGGAATCGCTT
CCTTCGCTGGCTCCATCTTCTCTCGCCTCGCTATGGGACCACTCTGTGAT
CTCATCGGACCACGTACTTCCTCAGCGATTCTCTCTTTTCTCACCGCTCC
TGTAATCCTCTCCGCCTCACTCGTCTCCTCTCCGACGTCCTTCATCCTCG
TCCGTTTCTTCGTCGGCTTCTCGCTCGCTAATTTCGTAGCCAATCAATAC
TGGATGTCCTCCATGTTCTCCGGTAACGTCATTGGTCTCGCTAACGGTGT
CTCAGCCGGTTGGGCTAACGTCGGCGCCGGTATCTCTCAGCTCCTTATGC
CTCTCATATACTCCACCATAGCCGAATTCCTTCCACGCGCCGTCGCCTGG
CGCGTGTCCTTCGTATTTCCCGCCATTTTTCAGGTTACAACGGCCGTCCT
CGTTCTCCTCTACGGCCAAGATACTCCCCACGGTAACAGAAAAAACTCGA
ACCAGAACAAACTCACAATTCCTGAAGAAGAAGAAGTACTAGTAGTTGAA
GAAGACGAACGTTCCAGTTTCGTCGAGATCCTAATCGGCGGACTTGGAAA
TTACAGAGCGTGGATCTTAGCGCTGCTCTACGGATACTCGTACGGCGTCG
AGCTAACGACGGACAACGTGATCGCCGGATATTTCTACGAGAGATTTGGA
GTGAATCTGGAGGCGGCGGGGACGATCGCGGCGAGTTTCGGGATATCGAA
CATTGCGTCGCGACCGGCGGGAGGGATGATATCGGATGCGCTGGGGAAGA
GATTCGGTATGAGAGGGAGGCTGTGGGGCTATGGATCGTGCAATCGGTG
GCTGGGTTGTTGTGCGTGTTACTCGGACGAGTCAACTCGCTCTGGGGATC
AATCCTCGTCATGTGGGTCTTCTCTGTTTTCGTTCAAGCTGCTTCTGGCC
TTGTATTTGGCGTGGTCCCTTTCGTCTCCACGCGGTCGTTAGGAGTGGTG
GCGGGAATTACGGGAAGCGGCGGTACGGTTGGTGCGGTGGTGACGCAGTT
TCTGTTGTTTTCCGGTGATGATGTTCGAAAACAGAGAAGCATTTCACTTA
TGGGTTTGATGACTTTTGTGTTTGCTCTTTCTGTTACATCAATTTACTTT
CCACAATGGGTGGAATGTGTTGTGGGCCTTCGTCATCTTCCGAAGAAGA
AGATATTTCTCGGGGACTCCTTGTAGAAGACGAAGATGAAGAAGGTAAAG
TGGTTAGTGGTAGTCTACGTCCCGTTTGTTGA
```

Accordingly, the coding sequence, which encodes the polypeptide having nitrate transporter activity, may comprise a nucleic acid sequence substantially as set out in SEQ ID No:3 or SEQ ID No:4, or a functional variant or fragment thereof. The inventors believe that the intron can increase the stability of the construct in vivo. Hence, the construct may not comprise SEQ ID No:4, i.e. the cDNA sequence encoding the *Arabidopsis* nitrate transporter.

The polypeptide sequence of *Arabidopsis* nitrate transporter is provided herein as SEQ ID No:5, follows:

```
                                          SEQ ID No: 5
MEPSQRNTKPPSFSDSTIPVDSDGRATVFRPFSLSSPHSRAFHLAWLSLF
SCFFSTFSIPPLVPVISSDLNLSASTVSAAGIASFAGSIFSRLAMGPLCD
LIGPRTSSAILSFLTAPVILSASLVSSPTSFILVRFFVGFSLANFVANQY
WMSSMFSGNVIGLANGVSAGWANVGAGISQLLMPLIYSTIAEFLPRAVAW
RVSFVFPAIFQVTTAVLVLLYGQDTPHGNRKNSNQNKLTIPEEEEVLVVE
EDERSSFVEILIGGLGNYRAWILALLYGYSYGVELTTDNVIAGYFYERFG
VNLEAAGTIAASFGISNIASRPAGGMISDALGKRFGMRGRLWGLWIVQSV
AGLLCVLLGRVNSLWGSILVMWVFSVFVQAASGLVFGVVPFVSTRSLGVV
AGITGSGGTVGAVVTQFLLFSGDDVRKQRSISLMGLMTFVFALSVTSIYF
PQWGGMCCGPSSSSEEEDISRGLLVEDEDEEGKVVSGSLRPVC
```

Accordingly, the polypeptide having nitrate transporter activity may comprise an amino acid sequence substantially as set out in SEQ ID No:5, or a functional variant or fragment thereof.

The inventors have created constructs in which the CERV promoter or the pea plastocyanin promoter has been used to drive expression of the nitrate transporter protein (NRT2.7) from *Arabidopsis thaliana*. This protein has been suggested as being involved in nitrate transport into the vacuole, and so was previously considered as being potentially involved in nitrate sequestering. However, the evidence is not conclusive. When the *Arabidopsis* ATNRT2.7 gene is over-expressed, it shows a strong phenotype in transformed plants, particularly during the onset of flowering. The inventors have found that over-expression of ATNRT2.7 using the constructs of the invention can considerably lower leaf nitrate content, and so can advantageously lower TSNA concentration in plants transformed with the constructs of the invention.

The construct may be capable of decreasing, in a plant transformed with a construct of the invention, the concentration of nitrate by at least 5%, 10%, 15%, 18%, 20%, 32%, 35%, 38%, 40%, 50%, 60% or 63% (as illustrated in FIGS. 2, 6 and 8), compared to the concentration of nitrate in the wild-type plant (i.e. which has not been transformed with a construct of the invention).

The construct may be capable of decreasing, in a plant transformed with the construct, the concentration of 4-(Methylnitrosamino)-1-(3-pyridyl)-1-butanone (NNK) by at least 10%, 20%, 30%, 40%, 50%, 60%, 61%, 62%, 65%, 69%, 71% or 75% (as illustrated in FIGS. 10-15), compared to the concentration of NNK in the wild-type plant.

The construct may be capable of decreasing, in a plant transformed with the construct, the concentration of N-Nitrosonornicotine (NNN) by at least 10%, 20%, 30%, 40%, 50%, 60%, 70%, 71%, 75%, 78%, 80%, 82%, 84%, 85%, 88%, 90% or 94% (as illustrated in FIGS. 10-15), compared to the concentration of NNN in the wild-type plant.

The construct may be capable of decreasing, in a plant transformed with the construct, the concentration of N-Nitrosoanatabine (NAT) by at least 5%, 6%, 10%, 20%, 23%, 24%, 30%, 40%, 46%, 45%, 48%, 50%, 60%, 70%, 80% or 85% (as illustrated in FIGS. 10-15), compared to the concentration of NAT in the wild-type plant.

The construct may be capable of decreasing, in a plant transformed with the construct, the concentration of total tobacco-specific nitrosamines (TSNA) by at least 10%, 20%, 30%, 40%, 50%, 56%, 60%, 64%, 65%, 70% or 75% (as illustrated in FIGS. 18-20), compared to the concentration of total TSNA in the wild-type plant.

Preferably, the construct is capable of decreasing the concentration of any of the compounds selected a group of compounds including nitrate, NNK, NNN, NAT and total TSNA, in a leaf or stem from a plant of a T0, T1 and/or T2 plant population. The construct may be capable of decreasing the concentrations of any of these compounds in a leaf located at a lower, middle or upper position on the plant. "Lower position" can mean in the lower third of the plant, "upper position" can mean in the upper third of the plant, and "middle position" can mean the central third of the plant between the lower and upper positions.

As shown in FIG. 24, the concentration of NNK in middle leaves of plants harbouring the PPC-AtNrt2.7 construct was below the level of detection. Accordingly, the construct may be capable of decreasing the concentration of NNK in a leaf located at a middle position on the plant.

Genetic constructs of the invention may be in the form of an expression cassette, which may be suitable for expression of the coding sequence encoding a nitrate transporter in a host cell. The genetic construct of the invention may be introduced in to a host cell without it being incorporated in a vector. For instance, the genetic construct, which may be a nucleic acid molecule, may be incorporated within a liposome or a virus particle. Alternatively, a purified nucleic acid molecule (e.g. histone-free DNA or naked DNA) may be inserted directly into a host cell by suitable means, e.g. direct endocytotic uptake. The genetic construct may be introduced directly in to cells of a host subject (e.g. a plant) by transfection, infection, microinjection, cell fusion, protoplast fusion or ballistic bombardment. Alternatively, genetic constructs of the invention may be introduced directly into a host cell using a particle gun. Alternatively, the genetic construct may be harboured within a recombinant vector, for expression in a suitable host cell.

Hence, in a third aspect, there is provided a recombinant vector comprising the genetic construct according to the first or second aspect.

The recombinant vector may be a plasmid, cosmid or phage. Such recombinant vectors are highly useful for transforming host cells with the genetic construct of the invention, and for replicating the expression cassette therein. The skilled technician will appreciate that genetic constructs of the invention may be combined with many types of backbone vector for expression purposes. The backbone vector may be a binary vector, for example one which can replicate in both *E. coli* and *Agrobacterium tumefaciens*. For example, a suitable vector may be a pBIN plasmid, such as pBIN19 (Bevan M., 1984, Nucleic Acids Research 12:8711-21).

Recombinant vectors may include a variety of other functional elements in addition to the promoter (e.g. a CERV or pea plastocyanin promoter), and the coding sequence encoding a nitrate transporter. For instance, the recombinant vector may be designed such that it autonomously replicates in the cytosol of the host cell. In this case, elements which induce or regulate DNA replication may be required in the recombinant vector. Alternatively, the recombinant vector may be designed such that it integrates into the genome of a host cell. In this case, DNA sequences which favour targeted integration (e.g. by homologous recombination) are envisaged.

The recombinant vector may also comprise DNA coding for a gene that may be used as a selectable marker in the cloning process, i.e. to enable selection of cells that have been transfected or transformed, and to enable the selection of cells harbouring vectors incorporating heterologous DNA. The vector may also comprise DNA involved with regulating expression of the coding sequence, or for targeting the expressed polypeptide to a certain part of the host cell, e.g. the chloroplast. Hence, the vector of the third aspect may comprise at least one additional element selected from a group consisting of: a selectable marker gene (e.g. an antibiotic resistance gene); a polypeptide termination signal; and a protein targeting sequence (e.g. a chloroplast transit peptide).

Examples of suitable marker genes include antibiotic resistance genes such as those conferring resistance to Kanamycin, Geneticin (G418) and Hygromycin (npt-II, hyg-B); herbicide resistance genes, such as those conferring resistance to phosphinothricin and sulphonamide based herbicides (bar and sit/ respectively; EP-A-242246, EP0369637A2); and screenable markers such as beta-glucuronidase (GB2197653), luciferase and green fluorescent protein (GFP). The marker gene may be controlled by a second promoter, which allows expression in cells, which may or may not be in the seed, thereby allowing the selection of cells or tissue containing the marker at any stage of development of the plant. Suitable second promoters are the promoter of nopaline synthase gene of *Agrobacterium* and the promoter derived from the gene which encodes the 35S cauliflower mosaic virus (CaMV) transcript. However, any other suitable second promoter may be used.

The various embodiments of genetic constructs of the invention may be prepared using the cloning procedure described in the Examples, which may be summarised as follows. The genomic or cDNA versions of the genes encoding the nitrate transporter may be amplified from the genomic or cDNA templates by PCR using suitable primers, for example SEQ ID No's 6 and 7. PCR products may then be examined using agarose gel electrophoresis. The PCR products may then be ligated into a suitable vector for cloning purposes, for example the pCR4Blunt-TOPO vector (Invitrogen). Vectors harbouring the PCR products may be grown up in a suitable host, such as *E. coli*. *E. coli* colonies may then be screened by PCR using suitable primers, and inserts in plasmids showing the correct restriction enzyme digest pattern may be sequenced using suitable primers.

*E. coli* colonies carrying TOPO-cDNA (AtNRT2.7) or TOPO-genomic DNA (AtNRT2.7) may be cultured to produce a suitable amount of each plasmid, which may then be purified. The plasmids may then be digested to release a DNA fragment encoding the AtNRT2.7, which may then be cloned into a vector harbouring a suitable promoter, for example either the CERV or pea plastocyanin (PPC) promoter, such as a pBNP plasmid (van Engelen et al., 1995, Transgenic Research, 4:288-290).

The resultant AtNRT2.7 constructs were named BNP-036AtNRT2.7001 (containing the pea plastocyanin promoter) and CRVAtNRT2.7 (containing the CERV promoter). Embodiments of the vector according to the third aspect may be substantially as set out in FIGS. 5a and 5b.

In view of their surprising results, the inventors believe that they are the first to have developed a method for decreasing nitrate concentrations in plant leaves using the expression of an exogenous nitrate transporter gene in a transgenic plant.

Hence, in a fourth aspect, there is provided a method of decreasing the nitrate concentration in the leaves of a test plant to below that of the corresponding nitrate concentration in leaves of a wild-type plant cultured under the same conditions, the method comprising altering plant metabolism in the test plant to achieve increased levels of a nitrate transporter in plant leaves.

In a fifth aspect of the invention, there is provided a method of producing a transgenic plant which transports nitrate out of a leaf at a higher rate than a corresponding wild-type plant cultured under the same conditions, the method comprising the steps of:—
(i) transforming a plant cell with the genetic construct according to the first or second aspect, or the vector according to the third aspect; and
(ii) regenerating a plant from the transformed cell.

In a sixth aspect, there is provided a method for producing a transgenic plant, the method comprising introducing, into an unmodified plant, an exogenous gene encoding a nitrate transporter, wherein expression of the nitrate transporter encoded by the exogenous gene reduces nitrate concentration in leaves of the transgenic plant relative to the concentration of nitrate in leaves of the unmodified plant.

In a seventh aspect, there is provided a transgenic plant comprising the genetic construct according to the first or second aspect, or the vector according to the third aspect.

In an eighth aspect, there is provided a transgenic plant comprising an exogenous gene encoding a nitrate transporter, wherein nitrate concentration in leaves of the transgenic plant is reduced compared to the nitrate concentration in leaves of an unmodified plant.

In a ninth aspect, there is provided use of an exogenous nucleic acid sequence encoding a nitrate transporter for reducing nitrate concentration in plant leaves by transformation of the plant with the exogenous nucleic acid sequence.

As described in Example 6, the inventors observed, in nitrate transporter over-expressing lines transformed with constructs of the invention that, as well as exhibiting reduced nitrate concentrations, the plant also develops chlorotic spots. These spots appear to be much more than mere "yellowing" which would be caused merely by a decrease in nitrate concentration, and in fact closely resemble leaf senescence. Thus, the inventors have demonstrated that transgenic expression of AtNRT2.7 in tobacco (using a constitutive promoter) is able to induce a senescence phenotype in tobacco leaves. Surprisingly, the senescence induction is specific to nitrate (i.e. 10 mM $NO_3$) and has not been observed in ammonium (10 mM $NH_4$), or lower concentrations. These results indicate therefore that AtNRT2.7 is not only able to lower nitrate content in the leaf, but can also trigger or accelerate a senescence-like phenotype. Although not wishing to be bound by hypothesis, the inventors believe that the vacuole may play a key role in the onset of senescence (e.g. in tobacco), as a consequence of lowering nitrate concentration. Thus, the inventors believe that the constructs of the invention can be used to prematurely induce plant senescence, or a senescence-like phenotype. Clearly, in certain plant species, such as tobacco, induction or acceleration of senescence is advantageous, for example for improving the flavour of smoked tobacco leaves.

Hence, in a tenth aspect, there is provided use of an exogenous nucleic acid sequence encoding a nitrate transporter for inducing senescence or a senescence-like phenotype in a test plant by transformation of the plant with the exogenous nucleic acid sequence.

Leaf senescence is a phase of plant development during which the cells undergo distinct metabolic and structural changes prior to cell death. Physiological and genetic studies indicate that senescence is a highly-regulated process. The progression of a leaf through senescence is visibly marked by the loss of chlorophyll and consequent yellowing, which results from the disassembly of the chloroplasts. The decreasing levels of leaf chlorophyll, characteristic of this developmental stage, can be measured, e.g. by solvent extraction and spectrophotometric measurement, or by a chlorophyll content meter. A decreased leaf chlorophyll level in comparison with an earlier leaf chlorophyll level recorded for the same plant, preferably grown under constant conditions, indicates senescence or a senescence-like phenotype.

Molecular studies indicate that senescence is associated with changes in gene expression. The levels of mRNAs encoding proteins involved in photosynthesis decrease during senescence, whilst mRNA levels of genes encoding proteins thought to be involved in the senescence increase. Senescence is a highly organised process regulated by genes known as Senescence Associated Genes (SAGs). Leaf senescence involves the degradation of proteins, nucleic acids and membranes, and the subsequent transport of the nutrients resulting from this degradation to other regions of the plant, such as the developing seeds, leaves or storage organs. Thus, any of these features may be measured using routine techniques to determine that senescence or a senescence-like phenotype has been induced prematurely.

The term "unmodified plant" can mean a plant before transformation with an exogenous gene or a construct of the invention. The unmodified plant may therefore be a wild-type plant.

The term "exogenous gene" can mean the gene that is transformed into the unmodified plant is from an external source, i.e. from a different species to the one being transformed. The exogenous gene may have a nucleic acid sequence substantially the same or different to an endogenous gene encoding a nitrate transporter in the unmodified plant. The exogenous gene may be derived from a genomic or cDNA sequence encoding a nitrate transporter from any species, such as the *Arabidopsis thaliana* NRT2.7 gene. The exogenous gene may form a chimeric gene, which may itself constitute a genetic construct according to the first or second aspect. The exogenous gene may encode a nitrate transporter having the amino acid sequence substantially as set out in SEQ ID No:5, or a functional variant or fragment thereof. The exogenous gene may comprise the nucleotide sequence substantially as set out in either SEQ ID No: 3 or 4, or a functional variant or fragment thereof.

Methods for determining the level of nitrate in plant leaves are set out in the Examples. The methods and uses of the invention may comprise transforming a test plant cell or unmodified plant cell with a genetic construct according to the first or second aspect, a vector according to the third aspect, or the exogenous gene described herein.

Thus, in an eleventh aspect, there is provided a host cell comprising the genetic construct according to the first or second aspect, or the recombinant vector according to the third aspect.

The cell may be a plant cell. The cell may be transformed with genetic constructs, vectors or exogenous genes according to the invention, using known techniques. Suitable means for introducing the genetic construct into the host cell may include use of a disarmed Ti-plasmid vector carried by *Agrobacterium* by procedures known in the art, for example as described in EP-A-0116718 and EP-A-0270822. A further method may be to transform a plant protoplast, which involves first removing the cell wall and introducing the nucleic acid, and then reforming the cell wall. The transformed cell may then be grown into a plant.

Preferably, and advantageously, the methods and uses according to the invention do not compromise the health or fitness of the test or transgenic plant that is generated. The inventors have observed that over-expressing the nitrate transporter (e.g. AtNRT2.7) in a plant host cell is effective at inducing nitrate transport from the plant's leaves, and preferably out of the vacuole of the plant's cells. Hence, it is preferred that the methods and uses of the invention comprise transforming the test plant with one or more constructs of the invention such that the nitrate transporter is over-expressed.

The transgenic or test plants according to invention may include the Brassicaceae family, such as *Brassica* spp. The plant may be *Brassica* napes (oilseed rape). Further examples of transgenic or test plants include the family Poales, such as *Triticeae* spp. The plant may be *Triticum* spp. (wheat). Increasing the grain protein content in wheat may result in increased volume of food products comprising wheat, such as bread.

Further examples of suitable transgenic or test plants according to the invention may include the Solanaceae family of plants which include, for example jimson weed, eggplant, mandrake, deadly nightshade (belladonna), *capsicum* (paprika, chilli pepper), potato and tobacco. One example of a suitable genus of Solanaceae is *Nicotiana*. A suitable species of *Nicotiana* may be referred to as tobacco plant, or simply tobacco.

Tobacco may be transformed with constructs, vectors and exogenous genes of the invention as follows.

*Nicotiana tabacum* is transformed using the method of leaf disk co-cultivation essentially as described by Horsch et al. (Science 227: 1229-1231, 1985). The youngest two expanded leaves may be taken from 7-week old tobacco plants and may be surface-sterilised in 8% Domestos™ for 10 minutes and washed 6 times with sterile distilled water. Leaf disks may be cut using a number 6 cork borer and placed in the *Agrobacterium* suspension, containing the appropriate binary vectors (according to the invention), for approximately two minutes. The discs may be gently blotted between two sheets of sterile filter paper. Ten disks may be placed on LS 3% sucrose+2 µM BAP+0.2 µM NAA plates, which may then be incubated for 2 days in the growth room. Discs may be transferred to plates of LS+3% sucrose+2 µM BAP+0.2 µM NAA supplemented with 500 g/l claforan and 100 g/l kanamycin. The discs may be transferred onto fresh plates of above medium after 2 weeks. After a further two weeks, the leaf disks may be transferred onto plates containing LS+3% sucrose+0.5 µM BAP supplemented with 500 mg/l claforan and 100 mg/l kanamycin. The leaf disks may be transferred onto fresh medium every two weeks. As shoots appear, they may be excised and transferred to jars of LS+3% sucrose supplemented with 500 mg/l claforan. The shoots in jars may be transferred to LS+3% sucrose+250 mg/l claforan after approximately 4 weeks. After a further 3-4 weeks the plants may be transferred to LS+3% sucrose (no antibiotics) and rooted. Once the plants are rooted they may be transferred to soil in the greenhouse.

In a twelfth aspect, there is provided a plant propagation product obtainable from the transgenic plant according to either the seventh or eighth aspect.

A "plant propagation product" may be any plant matter taken from a plant from which further plants may be produced. Suitably, the plant propagation product may be a seed. The plant propagation product may preferably comprise a construct or vector according to the invention or an exogenous gene.

The inventors have observed that a leaf of a test plant (i.e. a transgenic plant) which has been transformed with a construct according to the invention exhibits increases in nitrate remobilisation out of the leaf such that the concentration of nitrate, and thus TSNAs such as NNK, NNN and/or NAT decreases in that leaf. Clearly, such a leaf therefore would be particularly advantageous.

Therefore, in a thirteenth aspect of the invention, there is provided a harvested leaf containing a lower level of nitrate than the corresponding level of nitrate in a harvested leaf taken from a wild-type plant cultured under the same conditions, wherein the leaf is harvested from the transgenic plant according to either the seventh or eighth aspect, or produced by the method according to either the fifth or sixth aspect.

In a fourteenth aspect of the invention, there is provided a tobacco product comprising nitrate-reduced tobacco obtained from a mutant tobacco plant, which mutant is capable of decreasing the concentration of nitrate in its leaves.

It is preferred that the mutant tobacco plant from which the tobacco in the tobacco product is derived comprises a construct, vector or exogenous gene according to the invention.

The tobacco product may be smokeless tobacco product, such as snuff. The tobacco product may be an oral tobacco product deliverable by the mouth. The tobacco product may be moist, and may be snus. However, the tobacco product may also be a smoking article.

Thus, in a fifteenth aspect, there is provided a smoking article comprising nitrate-reduced tobacco obtained from a mutant tobacco plant, which mutant is capable of decreasing the concentration of nitrate in its leaves.

Nitrate-reduced tobacco can include tobacco in which the nitrate concentration is less than the corresponding concentration in a wild-type plant cultured under the same conditions. Such a smoking article may comprise tobacco obtained from a mutant tobacco plant, which may have been transformed with a genetic construct according to the first or second aspect of the invention, or a vector according to the third aspect, or an exogenous gene. Preferably, the mutant tobacco plant comprises the nitrate transporter, AtNRT2.7.

The term "smoking article" can include smokeable products, such as rolling tobacco, cigarettes, cigars and cigarillos whether based on tobacco, tobacco derivatives, expanded tobacco, reconstituted tobacco or tobacco substitutes and also heat-not-burn products.

It will be appreciated that the invention extends to any nucleic acid or peptide or variant, derivative or analogue thereof, which comprises substantially the amino acid or nucleic acid sequences of any of the sequences referred to herein, including functional variants or functional fragments thereof. The terms "substantially the amino acid/polynucleotide/polypeptide sequence", "functional variant" and "functional fragment", can be a sequence that has at least 40% sequence identity with the amino acid/polynucleotide/polypeptide sequences of any one of the sequences referred to herein, for example 40% identity with the gene identified as SEQ ID No.3 (which encodes one embodiment of a nitrate transporter), or 40% identity with the polypeptide identified as SEQ ID No.5 (i.e. one embodiment of a nitrate transporter).

Amino acid/polynucleotide/polypeptide sequences with a sequence identity which is greater than 65%, more preferably greater than 70%, even more preferably greater than 75%, and still more preferably greater than 80% sequence identity to any of the sequences referred to is also envisaged. Preferably, the amino acid/polynucleotide/polypeptide sequence has at least 85% identity with any of the sequences referred to, more preferably at least 90% identity, even more preferably at least 92% identity, even more preferably at least 95% identity, even more preferably at least 97% identity, even more preferably at least 98% identity and, most preferably at least 99% identity with any of the sequences referred to herein.

The skilled technician will appreciate how to calculate the percentage identity between two amino acid/polynucleotide/polypeptide sequences. In order to calculate the percentage identity between two amino acid/polynucleotide/polypeptide sequences, an alignment of the two sequences must first be prepared, followed by calculation of the sequence identity value. The percentage identity for two sequences may take different values depending on: (i) the method used to align the sequences, for example, ClustalW, Basic Local Alignment Search Tool (BLAST®), FASTA, Smith-Waterman (implemented in different programs), or structural alignment from 3D comparison; and (ii) the parameters used by the alignment method, for example, local vs global alignment, the pair-score matrix used (e.g. BLOSUM62, PAM250, Gonnet etc.), and gap-penalty, e.g. functional form and constants.

Having made the alignment, there are many different ways of calculating percentage identity between the two sequences. For example, one may divide the number of identities by: (i) the length of shortest sequence; (ii) the length of alignment; (iii) the mean length of sequence; (iv) the number of non-gap positions; or (iv) the number of equivalenced positions excluding overhangs. Furthermore, it will be appreciated that percentage identity is also strongly length dependent. Therefore, the shorter a pair of sequences is, the higher the sequence identity one may expect to occur by chance.

Hence, it will be appreciated that the accurate alignment of protein or DNA sequences is a complex process. The popular multiple alignment program ClustalW (Thompson et al., 1994, Nucleic Acids Research, 22, 4673-4680; Thompson et al., 1997, Nucleic Acids Research, 24, 4876-4882) is a preferred way for generating multiple alignments of proteins or DNA in accordance with the invention. Suitable parameters for ClustalW may be as follows: For DNA alignments: Gap Open Penalty=15.0, Gap Extension Penalty=6.66, and Matrix=Identity. For protein alignments: Gap Open Penalty=10.0, Gap Extension Penalty=0.2, and Matrix=Gonnet. For DNA and Protein alignments: ENDGAP=−1, and GAPDIST=4. Those skilled in the art will be aware that it may be necessary to vary these and other parameters for optimal sequence alignment.

Preferably, calculation of percentage identities between two amino acid/polynucleotide/polypeptide sequences is then calculated from such an alignment as $(N/T)*100$, where N is the number of positions at which the sequences share an identical residue, and T is the total number of positions compared including gaps but excluding overhangs. Hence, a most preferred method for calculating percentage identity between two sequences comprises (i) preparing a sequence alignment using the ClustalW program using a suitable set of parameters, for example, as set out above; and (ii) inserting the values of N and T into the following formula:—Sequence Identity $=(N/T)*100$.

Alternative methods for identifying similar sequences will be known to those skilled in the art. For example, a substantially similar nucleotide sequence will be encoded by a sequence which hybridizes to the sequences shown in SEQ ID Nos. 1, 2 or 3, or their complements under stringent conditions. By stringent conditions, we mean the nucleotide hybridises to filter-bound DNA or RNA in 3× sodium chloride/sodium citrate (SSC) at approximately 45° C. followed by at least one wash in 0.2×SSC/0.1% SDS at approximately 20-65° C. Alternatively, a substantially similar polypeptide may differ by at least 1, but less than 5, 10, 20, 50 or 100 amino acids from the sequences shown in SEQ ID No. 5.

Due to the degeneracy of the genetic code, it is clear that any nucleic acid sequence could be varied or changed without substantially affecting the sequence of the protein encoded thereby, to provide a functional variant thereof. Suitable nucleotide variants are those having a sequence altered by the substitution of different codons that encode the same amino acid within the sequence, thus producing a silent change. Other suitable variants are those having homologous nucleotide sequences but comprising all, or portions of, sequence, which are altered by the substitution of different codons that encode an amino acid with a side chain of similar biophysical properties to the amino acid it substitutes, to produce a conservative change. For example small non-polar, hydrophobic amino acids include glycine, alanine, leucine, isoleucine, valine, proline, and methionine. Large non-polar, hydrophobic amino acids include phenylalanine, tryptophan and tyrosine. The polar neutral amino acids include serine, threonine, cysteine, asparagine and glutamine. The positively charged (basic) amino acids include lysine, arginine and histidine. The negatively charged (acidic) amino acids include aspartic acid and glutamic acid. It will therefore be appreciated which amino acids may be replaced with an amino acid having similar biophysical properties, and the skilled technician will known the nucleotide sequences encoding these amino acids.

All of the features described herein (including any accompanying claims, abstract and drawings), and/or all of the steps of any method or process so disclosed, may be combined with any of the above aspects in any combination, except combinations where at least some of such features and/or steps are mutually exclusive.

For a better understanding of the invention, and to show how embodiments of the same may be carried into effect, reference will now be made, by way of example, to the accompanying Figures, in which:—

FIG. 1 shows the chemical structures of various tobacco smoke nitrosamines, 4-(Methylnitrosamino)-1-(3-pyridyl)-1-butanone (NNK), N-Nitrosonornicotine (NNN), N-Nitrosoanabasine (NAB) and N-Nitrosoanatabine (NAT);

FIG. 2 is a graph showing the green leaf nitrate content of various $T_0$ green house populations of *Nicotiana tobacum* plants and transformed with PPC-Nrt2.7 constructs generated, i.e. constructs containing the nitrate transporter 2.7 gene under the control of the pea plastocyanin promoter. The values for the individual plants of each population are shown in FIGS. 3 and 4;

FIG. 3 shows the concentration of nitrate in green leaves of *Nicotiana tabacum* c.v. Burley populations ($T_0$) harbouring the leaf specific promoter PPC::NRT2.7 construct (Wild-type Burley lines acted as control);

FIG. 4 is a graph showing the concentration of nitrate in green leaves of *Nicotiana tabacum* c.v. Virginia populations ($T_0$) containing the PPC promoter::NRT2.7 construct;

FIG. 5*a* is a plasmid map of one embodiment of a construct according to the invention, known as BNP036AtNRT2.7001. The construct includes the AtNRT2.7 nitrate transporter gene under the control of the pea plastocyanin (PPC) promoter;

FIG. 5b is a plasmid map of another embodiment of a construct according to the invention, known CRVAtNRT2.7. The construct includes the AtNRT2.7 nitrate transporter gene under the control of the CERV promoter;

FIG. 6 shows the average concentration of nitrate in leaves of *Nicotiana tabacum* c.v. Burley populations ($T_0$) having the CRV::NRT2.7 construct, i.e. constructs containing the nitrate transporter 2.7 gene under the control of the constitutive CRV promoter. Wild-type Burley lines acted as control. The values for the individual plants of each population are shown in FIG. 7;

FIG. 7 shows the concentration of nitrate in leaves of *Nicotiana tabacum* c.v. Burley populations. ($T_0$) having the constitutive promoter CRV::NRT2.7 construct (Wild-type Burley lines acted as control;

FIG. 8 shows the concentration of nitrate in leaves of *Nicotiana tabacum* c.v. Burley populations ($T_1$) having the constitutive promoter CRV::NRT2.7 construct (Wild-type Burley lines acted as control). The values for the individual plants of each population are shown in FIG. 9;

FIG. 9 shows the concentration of nitrate in green leaves of *Nicotiana tabacum* c.v. Burley populations ($T_1$) containing the constitutive CRV promoter::Nrt2.7 construct. Wild-type plants acted as control;

FIG. 10 shows the concentration of blend TSNAs in upper leaves of *Nicotiana tabacum* c.v. Burley populations ($T_2$) containing the constitutive promoter CERV::AtNrt2.7 construct. These populations were grown on a low nitrate regime. Wild-type plants acted as the control. The legend "NAT, NNK, NNN" refers to the individual nitrosamine levels;

FIG. 11 shows the concentration of blend TSNAs in upper leaves of *Nicotiana tabacum* c.v. Burley populations ($T_2$) containing the constitutive promoter CERV::AtNrt2.7 construct. These populations were grown on a high nitrate regime. Wild-type plants acted as the control;

FIG. 12 shows the concentration of blend TSNAs in mid leaves of *Nicotiana tabacum* c.v. Burley populations ($T_2$) containing the constitutive promoter CERV::AtNrt2.7 construct. These populations were grown on a low nitrate regime. Wild-type plants acted as the control;

FIG. 13 shows the concentration of blend TSNAs in mid leaves of *Nicotiana tabacum* c.v. Burley populations ($T_2$) containing the constitutive promoter CERV::AtNrt2.7 construct. These populations were grown on a high nitrate regime. Wild-type plants acted as the control;

FIG. 14 shows the concentration of blend TSNAs in lower leaves of *Nicotiana tabacum* c.v. Burley populations ($T_2$) containing the constitutive promoter CERV::AtNrt2.7 construct. These populations were grown on a low nitrate regime. Wild-type plants acted as the control;

FIG. 15 shows the concentration of blend TSNAs in lower leaves of *Nicotiana tabacum* c.v. Burley populations ($T_2$) containing the constitutive promoter CERV::AtNrt2.7 construct. These populations were grown on a high nitrate regime. Wild-type plants acted as the control;

FIG. 16 shows the concentration of N-Nitrosonornicotine (NNN) in cured leaves of *Nicotiana tabacum* c.v. Burley populations grown in the field. Harvested leaves were taken from three positions of the plant, i.e. Upper Leaf, Middle Leaf and Lower Leaf as shown in the legend;

FIG. 17 shows the concentration of N-Nitrosonornicotine (NNN) in cured leaves of *Nicotiana tabacum* c.v. Burley populations grown in the field. Harvested leaves were taken from three positions of the plant, i.e. Upper Leaf, Middle Leaf and Lower Leaf;

FIG. 18 shows the concentration total blend TSNAs in cured lower leaves of *Nicotiana tabacum* c.v. Burley populations ($T_2$, CRV-AtNrt2.7) grown on 10 g/l nitrate "high nitrate" and 4 g/l "low nitrate" as shown in the legend. Wild-type acted as the control;

FIG. 19 shows the concentration of total blend TSNAs in cured mid leaves of *Nicotiana tabacum* c.v. Burley populations ($T_2$, CRV-AtNrt2.7) grown on 10 g/l nitrate "high nitrate" and 4 g/l "low nitrate". Wild-type acted as the control;

FIG. 20 shows the concentration of total blend TSNAs in cured upper leaves of *Nicotiana tabacum* c.v. Burley populations ($T_2$, CRV-AtNrt2.7) grown on 10 g/l nitrate "high nitrate" and 4 g/l "low nitrate". Wild-type acted as the control;

FIG. 21 shows gel images of RTPCR results from Burley populations of PPC-AtNrt2.7 and CRV-AtNrt2.7. The samples are part of a screen carried out on sibling populations of each transformant. FIG. 21a are the results when the samples were PCR'd after the RTPCR phase had been completed (using SupercriptIII) and the total RNA had been converted to cDNA. Therefore, the presence of bands in lanes demonstrated expression of AtNrt2.7 in those samples. FIG. 21b shows the results when the total RNA was PCR'd without the RTPCR step. This confirms that there is no DNA contamination which would lead to false positives in the samples;

FIG. 22 shows the alignment of the nucleotide sequences of the CRV promoter. (SEQ ID NO: 1) with the CamV35s promoter (SEQ ID NO: 10);

FIG. 23 shows the concentration of N-Nitrosonornicotine (NNN) in smoke derived from field-grown Virginia tobacco harbouring the PPC-AtNrt2.7 construct;

FIG. 24 shows the concentration of 4-(Methylnitrosamino)-1-(3-pyridyl)-1-butanone (NNK) (NNK) in smoke derived from field-grown Virginia tobacco harbouring the PPC-AtNrt2.7 construct. Only upper and lower leaves are shown, since NNK levels in the middle leaf were undetectable;

FIG. 25 shows the concentration of NNN from Burley tobacco plants harbouring the CRV-AtNrt2.7 construct, which have been grown on 10 mM Nitrate; and FIG. 26 shows the concentration of NNN from Burley tobacco plants harbouring the CRV-AtNrt2.7 construct, which have been grown on 10 mM Ammonia.

EXAMPLES

The inventors have developed constructs and transgenic plants in which the concentration of nitrate and various TSNAs was significantly decreased upon expression of a nitrate transporter gene (*Arabidopsis thaliana* NRT2.7) under the control of either: (a) the constitutive promoter, Carnation Etched Ring Virus (CERV) promoter (Hull et al., 1986, EMBO J., 5, 3083-3090); or (b) the leaf-specific promoter, pea-plastocyanin (PPC).

Example 1

Isolation of *Arabidopsis* Nitrate Transporter Genes

The *Arabidopsis thaliana* nitrate transporter gene used in these experiments was AtNRT2.7.
Design of Primers
The full length genomic sequence coding for the nitrate transporter 2.7 from *A. thaliana* was identified (Accession Number for the sequence was: T15N1-60). Primers for use in PCR to isolate the genomic sequence were designed, which were tailed at the 5' end with a 4 by spacer and suitable restriction sites. SacI and BamHI restriction sites were generated at the 5' end, and KpnI and SacI restriction sites were generated at the 3' end of the fragment, to enable the cloning of the fragments into appropriate vectors. The sequences of these primers are shown below:

AtNRT2.7 (T15F)
[SEQ ID NO. 6]
ATC GAG CTC GGA TCC ATG GAG CCA TCT CAA CGC AAC

ACC

AtNRT2.7 (T15R)
[SEQ ID NO. 7]
ATC GAG CTC GGT ACC ACA AAC GGG ACG TAG ACT ACC

It will be appreciated by the skilled person that other PCR primers could be designed incorporating the required features of the primers and alternative restriction enzyme sites.

Isolation of *Arabidopsis* Genomic DNA Encoding NRT2.7

*Arabidopsis thaliana* var. *Columbia* genomic DNA was extracted from the rosette leaves of 3-week old plants using the Qiagen DNA Easy miniprep extraction kit. Briefly, genomic DNA was extracted from leaf samples using a QIAGEN DNeasy Plant DNA extraction kit (#69106) (QIAGEN Ltd., Crawley, UK), following the manufacturer's instructions. This method provided large amounts of very clean DNA suitable for gene isolation and cloning strategies. The principle of the kit utilises the specific absorption of DNA under high salt conditions to a silica-gel based membrane whilst contaminants such as proteins, carbohydrates, polyphenolics and other plant metabolites, are washed away.

Isolation of Nitrate Transporter DNA Fragments

The genomic sequence of *Arabidopsis* NRT2.7 is 1893 bp long (accession number T15N1-60). Genomic *Arabidopsis* NRT2.7 was amplified with primer pairs T15F (SEQ ID NO.6) and T15R (SEQ ID NO.7), which generated SacI and BamHI restriction sites at the 5' end and KpnI and SacI restriction sites at the 3' end of the fragment.

PCR Conditions:

In 25 μl reaction volume, 0.5 μl proof reading TAQ polymerase; 0.5 μl TAQ extender; 0.5 μl *Arabidopsis* genomic DNA; 0.25 μl forward primer; 0.25 μl reverse primer; 2.5 μl TAQ extender buffer; 2.5 μl dNTPs; 18 μl water, was added; annealing at 55° C. extended for 72° C. for 2 mins, 30 cycles.

An aliquot of the PCR reaction was then analysed by agarose gel electrophoresis. Reactions were precipitated and then stored. Nitrate transporter DNA fragments were then cloned into pTOPO vectors (available from Invitrogen), as described below.

Ligation Reactions:

1 μl TOPO was taken with 1 μl salt solution, and 4 μl PCR reaction. The mixture was left at room temperature for 30 mins. 2 μl of the ligation reaction mixture were taken with TOP10 *E. coli* cells, and then left on ice for 30 mins. The cells were heat-shocked at 42° C. for 30 s, and then left on ice for 5 min. The cells were then incubated in 250 μl SOC media at 37° C. for 30 mins. The cells were then plated onto agar plates containing Kanamycin and left overnight at 37° C. Cells containing plasmids grew into colonies, and about 50 colonies were observed for each gene sequence. Colony PCR was used to select individual clones containing the pTOPO vector with successfully inserted genomic DNA fragments.

Colonies were picked into 50 μl of 2YT+Kanamycin and allowed to grow for 1 hr at 37° C. In 10 μl PCR reaction, 1 μl dNTPs, 1 μl buffer, 0.1 μl forward primer (M13F), 0.1 μl reverse primer (M13R), 0.3 μl TAQ, and 7.5 μl water. Three colonies were picked for each sequence containing the expected sized PCR fragment. Individual colonies were then grown up and plasmid DNA was extracted for sequence analysis.

Sequence Analysis

The nitrate transporter DNA fragments present in a number of independent pTOPO clones were sequenced. Analysis of the sequence showed that the clones contained the nitrate transporter 2.7 gene.

Example 2

Construction of Vectors for Tobacco Transformation

Cloning of Genomic DNA Encoding AtNRT 2.7 into a Binary Vector pTOPO plasmids containing the NRT 2.7 gene were digested with KpnI and BamHI to isolate the NRT2.7 gene fragment, which was then cloned into pBNP binary vectors (pBNP-PPC-nosT), which had also been digested with KpnI and BamHI, and subsequently transformed into *E. coli* electrocompetent cells. The pBNP vector is an in-house vector created from the pBNP binary vector (van Engelen et al., 1995, Transgenic Research, 4:288-290), containing the PPC promoter and the nopaline synthase terminator. Cells containing the plasmid were selected on kanamycin plates. Clones were then isolated and the DNA was extracted and analysed by restriction digestion followed by sequencing.

The CERV is a constitutive promoter of the caulimovirus group of plant viruses. It was isolated and characterised in 1986 by Hull et al. and is characteristic of CaMV (Hull et al., 1986), but has little sequence similarity with the CaMV 35S promoter (see FIG. 23).

The pea plastocyanin promoter was isolated by Helliwell and Gray (1995, Plant Molecular Biology 29(3):621-626), and has demonstrated through expression studies that it is specific to the leaf.

The following binary vectors were produced:
(i) pBNP036AtNRT2.7001 (see FIG. 5a): pea plastocyanin promoter: Nrt2.7 cDNA: Nos terminator; and
(ii) pBNPCRVAtNRT2.7 (see FIG. 5b): Carnation Etch Ring Virus (CERV) promoter: Nrt2.7 cDNA: Nos terminator.

These two binary vectors were then transformed into *Agrobacterium tumefaciens* LBA 4404 by electroporation. This was performed by mixing 40 !al of *A. tumefaciens* electrocompetent cells and 0.5 μg of plasmid DNA, and placing in a pre-cooled cuvette. The cells were then electroporated at 1.5 Volts, 600 Ohms and 25 μFD. 1 ml of 2YT media was added to the cuvette and the mixture was decanted into a 30 ml universal container and incubated at 28° C. for 2 hours in a shaking incubator. 100 μl of cells were then plated onto kanamycin (50 μg/ml) and streptomycin (100 μg/ml) LB agar plates. The plates were left to incubate for 2 days at 28° C.

Example 3

Transformation of Tobacco

*Nicotiana tabacum* c.v. Vir40 and *Nicotiana tabacum* c.v. Burley 52 were transformed with pBNP036AtNRT2.7001 or pBNPCRVAtNRT2.7 using the method of leaf disk co-cultivation, as described by Horsch et al. (Science 227: 1229-1231, 1985). The youngest two expanded leaves were taken from 7-week old tobacco plants and were surface-sterilised in 8% Domestos for 10 minutes and washed 6 times with sterile distilled water. Leaf disks were then cut using a number 6 cork borer and placed in the *Agrobacterium* suspension for approximately two minutes. The discs were then gently blotted between two sheets of sterile filter paper. 10 disks were placed on LS 3% sucrose+2 μM BAP+0.2 μM NAA plates, which were then incubated for 2 days in the growth room. Discs were then transferred to plates of LS+3% sucrose+2 µM BAP+0.2 µM NAA supplemented with 500 g/l claforan and 100 g/l kanamycin.

The discs were transferred onto fresh plates of the above medium after 2 weeks. After a further two weeks the leaf disks were transferred onto plates containing LS+3% sucrose+0.5 µM BAP supplemented with 500 mg/l claforan and 100 mg/l kanamycin. The leaf disks were transferred onto fresh medium every two weeks. As shoots appeared, they were excised and transferred to jars of LS+3% sucrose supplemented with 500 mg/l claforan. The shoots in jars were transferred to LS+3% sucrose+250 mg/l claforan after approximately 4 weeks. After a further 3-4 weeks, the plants were finally transferred to LS+3% sucrose (no antibiotics) and rooted. Once the plants were rooted they were transferred to soil in the greenhouse.

Example 4

Analysis of Transformed Plants for the Presence of the AtNRT2.7 Constructs

Analysis of Regenerated Tobacco Transformants

Leaf material was taken from regenerated tobacco plants and genomic DNA was isolated. One large tobacco leaf (approximately 30 mg) was excised from an in vitro grown plant and placed in a 1.5 ml Eppendorf tube. The tissue was homogenised using a micropestle and 400 µl extraction buffer (200 mM Tris HCL pH 8.0; 250 mM NaCl; 25 mM EDTA; 0.5% SDS; 40 µg/ml Rnase A) was added and ground again carefully to ensure thorough mixing. Samples were vortex-mixed for approximately 5 seconds and then centrifuged at 10,000 rpm for 5 minutes. A 350 µl aliquot of the resulting supernatant was placed in a fresh Eppendorf tube and 350 µl chloroform was added. After mixing, the sample was allowed to stand for 5 minutes. This was then centrifuged at 10,000 rpm for 5 minutes. A 300 µl aliquot of the supernatant was removed into a fresh Eppendorf tube. To this, 300 µl of propan-2-ol was added and mixed by inverting the Eppendorf several times. The sample was allowed to stand for 10 minutes. The precipitated DNA was collected by centrifuging at 10,000 rpm for 10 minutes. The supernatant was discarded and the pellet air dried. The pellet of DNA was resuspended in 50 µl of distilled water and was used as a template in Q PCR. 30 plants of each construct/variety type were analysed by QPCR to check for transgenic events.
Results ($T_0$):

| pBNP036AtNRT2.7001: Virginia | 9 single copies |
| pBNP036AtNRT2.7001: Burley | 7 single copies |
| pBNPCRVAtNRT2.7: Burley | 10 single copies |

Example 5

Analysis of Transformed Plants for Nitrate Transporter Expression mRNA Levels Assayed by RTPCR Total RNA was isolated from tobacco leaf discs using the Ambion RNAqueous kit (Ambion Inc., Canada). All frozen samples were ground under liquid nitrogen to a fine powder using a tissuelyser. Extracellular membranes, polysaccharides and high molecular weight DNA were precipitated by centrifugation at 13,000 rpm for 5 minutes at 4° C. The supernatant was transferred to the filter cartridge supplied with the kit and centrifugation used to wash and purify the RNA which is then eluted with elution buffer. RNA samples were stored at −80° C. until further use.

RTPCR was performed on the total RNA using Invitrogen's 1-step RTPCR superscript III (see FIG. 21a). The resulting cDNA was then amplified with primers specific for AtNrt2.7 (SEQ ID No's: 8 and 9) to establish gene expression.

```
                                           [SEQ ID NO. 8]
GCGCCGGTATCTCTCAGCTCCTTA = RTPCR primer sequence
RTP0068F2

[SEQ ID NO. 9]
ATATCATCCCTCCCGCCGGT = RTPCR primer sequence
RTP0068R2
```

Controls were carried out using RNA without the RT reaction to confirm there was no DNA contamination, as shown in FIG. 21b. Wild-type controls were run alongside transgenic lines and plasmid control to give correct band size.

Example 6

Tobacco Phenotype $T_0$ Phenotype of AtNRT2.7 (pBNP036AtNRT2.7001: Burley) displayed chlorotic spots on the oldest leaves, when the plants were approximately 12 weeks old. These spots gradually increased in the leaves up the plant coinciding with senescence of the leaves. A brown stain was also observed along the main stem of the plants. The phenotype was observed in 70% of the transformants. This phenotype was also observed in the $T_1$ populations and the $T_2$ populations.

Example 7

Analysis of Tobacco Leaf for Nitrate Content

Determination of Nitrate in Plant Tissue

This method for determining nitrate concentrations in plant tissues is described in several papers including the Masclaux paper (Planta (2000) 211, pp 510-518). It relies on the nitration of salicylic acid by the nitrate in the plant extract under highly acidic conditions and the complex formed absorbs maximally at 410 nm. The chromaphore formed is 5-nitrosalicylic acid. This method has been shown to be sensitive and has little interference from chloride, nitrite and ammonium ions (Cataldo D. A., Community Soil Science and Plant Analysis, 6 (1), pp 71-80, 1975).

Materials are:

Extraction Buffer: 50 mM Phosphate buffer pH7.5; Assay Solution: 5% Salicylic acid in Sulphuric Acid (conc); Also required: 2N Sodium Hydroxide Method: Firstly, 100 mg of tissue was ground down in liquid nitrogen, and 300 µl of extraction buffer was then added and homogenized. The homogenate was centrifuged at 30 g for 15 mins at 4° C. and the supernatant was then removed for analysis. 10 µl of the supernatant was mixed with 40 µl assay solution in a 1 ml assay plate (blank controls were set up at same time). The reaction was incubated at room temperature for 20 mins, and 950 µl of 2N Sodium Hydroxide was slowly added to raise the pH above 12. The samples were cooled to room temperature and the absorbance at 410 nm was determined (decant 250 μl into a titretek plate to read). Standards of 100 mM, 50, 40, 30, 20, 10, 5 and 1 potassium nitrate were also measured.

Fresh tissue samples (i.e. not freeze dried or oven-dried) and a separate blank were required because of pigmentation of extracts. This consisted of extract, 40 μl of sulphuric acid (no salicylic acid) and 1950 μl of 2N sodium hydroxide. The nitrate standards were stored at 4° C.

The nitrate results illustrated in FIGS. 2 to 9 show that there is a lowering of leaf nitrate concentration in the transformed plants with both the CRV-AtNrt2.7 and PPC-AtNrt2.7 constructs of the invention. Although they do not wish to be bound by theory, the inventors hypothesise that the AtNrt2.7 protein is acting as a nitrogen remobiliser and shuttling nitrate out of the vacuoles to sink areas in the plants, such as seed development. This results in the leaves being depleted of nitrate, and leads to chlorosis as shown by the phenotype.

Example 8

Analysis of Cured Leaf for TSNA Content

The TSNA results shown in FIGS. 10 to 27 show a considerable reduction in total TSNA concentration (i.e. NAT, NNK and NNN) as a result of the AtNrt2.7 construct. This is hypothesised to be related to less residual leaf nitrate at the time of harvest. Nitrate is one of the major precursors for TSNA production in cured tobacco leaves (Staaf et al., 2005, Contributions to Tobacco Research, 21:321-330; de Roton et al., 2005, Contributions to Tobacco Research, 21:305-320). Therefore, lower levels of nitrate in the leaves as seen in the T0 and T1 populations would lead to lower levels of TSNAs in the cured leaf. Burley in particularly has high levels of NNN and, when these plants were grown in the field, the NNN levels showed a decrease.

FIGS. 23 and 24 show that NNN and NNK levels, respectively, are decreased in upper, middle and lower leaves of field-grown plants that harbour the PPC-AtNrt2.7 construct. Furthermore, as shown in FIG. 24, middle leaf NNK concentrations for PPC-AtNrt2.7 cell lines were all below the level of detection, and so are not shown in this graph.

FIGS. 25 and 26 show blend NNN levels from greenhouse-grown Burley plants that harbour the CRV-AtNrt2.7 construct, when grown on either 10 mM nitrate (FIG. 25) or 10 mM ammonia (FIG. 26). These data demonstrate that the decrease in NNN concentrations is specific to the transport of nitrate, caused by over-expression of the nitrate transporter, AtNrt2.7. This is because, as shown in FIG. 25, both of the test plants (labelled '43' and '45') show decreased concentrations due to being grown on nitrate, whereas, as shown in FIG. 26, neither test plant showed a decrease in NNN when grown on ammonia, which would not have been affected by over-expression of the nitrate transporter gene, AtNrt2.7.

The invention claimed is:

1. A tobacco product comprising nitrate-reduced tobacco obtained from a mutant tobacco plant, the mutant tobacco plant comprising a genetic construct comprising a promoter operably linked to a coding sequence encoding an NRT2.7 nitrate transporter polypeptide having nitrate transporter activity, wherein the promoter is not a cauliflower mosaic virus 35S promoter, and wherein the promoter is selected from the group consisting of Carnation Etch Ring Virus (CERV) promoter, pea plastocyanin promoter, rubisco promoter, nopaline synthase promoter, chlorophyll a/b binding promoter, high molecular weight glutenin promoter, α, β-gliadin promoter, hordein promoter, patatin promoter, and a senescence-specific promoter, and wherein the coding sequence, which encodes the polypeptide having nitrate transporter activity, comprises a nucleic acid sequence as set out in SEQ ID NO:3 or SEQ ID NO:4, or a sequence with 90% identity with SEQ ID NO:3 or SEQ ID NO:4 wherein a population of said mutant tobacco plants with said genetic construct has an average lower leaf nitrate content than a population of plants without said construct.

2. The tobacco product according to claim 1, wherein the tobacco product is one of a smokeless tobacco product, an oral tobacco product deliverable by mouth, or a smoking article.

3. A smoking article comprising nitrate-reduced tobacco obtained from a mutant tobacco plant, wherein the mutant tobacco plant is capable of decreasing the concentration of nitrate in its leaves, said mutant tobacco plant comprising a genetic construct comprising a promoter operably linked to a coding sequence encoding an NRT2.7 nitrate transporter polypeptide having nitrate transporter activity, wherein the promoter is not a cauliflower mosaic virus 35S promoter, and wherein the promoter is selected from the group consisting of Carnation Etch Ring Virus (CERV) promoter, pea plastocyanin promoter, rubisco promoter, nopaline synthase promoter, chlorophyll a/b binding promoter, high molecular weight glutenin promoter, α, β-gliadin promoter, hordein promoter, patatin promoter, and a senescence-specific promoter, and wherein the coding sequence, which encodes the polypeptide having nitrate transporter activity, comprises a nucleic acid sequence as set out in SEQ ID NO:3 or SEQ ID NO:4, or a sequence with at least 90% identity with SEQ ID NO:3 or SEQ ID NO:4 wherein a population of said mutant tobacco plants with said genetic construct has an average lower leaf nitrate content than a population of plants without said construct.

4. The smokeless tobacco product according to claim 2, wherein the smokeless tobacco product is snuff.

5. The oral tobacco product deliverable by mouth according to claim 2, wherein the oral tobacco product deliverable by the mouth is snus.

\* \* \* \* \*

SEQUENCE LISTING

```
<160> NUMBER OF SEQ ID NOS: 10

<210> SEQ ID NO 1
<211> LENGTH: 232
<212> TYPE: DNA
<213> ORGANISM: Carnation etched ring virus

<400> SEQUENCE: 1
agcttgcatg cctgcaggtc gagcttttag gattccatag tgataagata tgttcttatc      60
taaacaaaaa agcagcgtcg gcaaaccata cagctgtcca caaaaaggaa aggctgtaat     120
aacaagcgga cccagcttct cagtggaaga tactttatca gacactgaat aatggatgga     180
ccctaccacg attaaagagg agcgtctgtc taaagtaaag tagagcgtct tt             232

<210> SEQ ID NO 2
<211> LENGTH: 783
<212> TYPE: DNA
<213> ORGANISM: Pisum sativum

<400> SEQUENCE: 2
tatgcaactt acaacgtgca ctcgcggagg attggacgtg tgcaacttac aacgtacgca      60
ttgttcgttc atacaatagt gtagaattgg acatgtgcaa cttacaacat gtgcaactta     120
caacgtgcgc tcgcggagga atgtgaagtt gaacacgtac aacttacgtc atttgtgcat     180
gcagaagcat agagctgagc acacaattca taatttgaag gacacatgat ttgctataaa     240
gaactcttta gaagtaccac aactttgact gagtttgata tagctaataa agatggagct     300
cattataatt tgaatggcat aatcaagcta aacgaacaag cttagttaat catgttaaac     360
aacaattctt tgtaataata aattgtcttt caactagtcc aagtttatga gttgattctt     420
cggaataaat tagaaaatat cttagatttt atacttcatt gattatttca tagagcaagt     480
aggagaaata aaaatatact agtattattt actaaaaaaa atctaagcca cgtcggagga     540
```

| taacatccaa | cccagccaat | cacagcaatg | ttcatcagat | aacccacttt | aagcccacgc | 600 |
| actctgtggc | acatctacat | tatctaaatc | acatattctt | ccacacatct | tagccacaca | 660 |
| aaaacccaat | ccacatcttt | atcatccatt | ctataaaaaa | tcaccttctg | tgtgtctctc | 720 |
| tttcgattcc | cttcaaacac | atacaaattc | agtagagaag | aaactcatta | ctcttgagaa | 780 |
| aaa | | | | | | 783 |

<210> SEQ ID NO 3
<211> LENGTH: 1560
<212> TYPE: DNA
<213> ORGANISM: Arabidopsis thaliana

<400> SEQUENCE: 3

| atggagccat | ctcaacgcaa | caccaaaccg | ccgtcgtttt | cagattccac | tatcccggtt | 60 |
| gattccgatg | gtcgagccac | cgtcttccga | ccattctctc | tcctcgcc | acactcacga | 120 |
| gcctttcacc | tagcttggct | ctcactcttc | tcatgcttct | tctccacctt | ctccatccct | 180 |
| cctctggtcc | ccgtcatctc | ctccgacctc | aacctctctg | cctccaccgt | atccgccgcc | 240 |
| ggaatcgctt | ccttcgctgg | ctccatcttc | tctcgcctcg | ctatgggacc | actctgtgat | 300 |
| ctcatcggac | cacgtacttc | ctcagcgatt | ctctcttttc | tcaccgctcc | tgtaatcctc | 360 |
| tccgcctcac | tcgtctcctc | tccgacgtcc | ttcatcctcg | tccgtttctt | cgtcggcttc | 420 |
| tcgctcgcta | atttcgtagc | caatcaatac | tggatgtcct | ccatgttctc | cggtaacgtc | 480 |
| attggtctcg | ctaacggtgt | ctcagccggt | tgggctaacg | tcggcgccgg | tatctctcag | 540 |
| ctccttatgc | ctctcatata | ctccaccata | gccgaattcc | ttccacgcgc | cgtcgcctgg | 600 |
| cgcgtgtcct | tcgtatttcc | cgccattttt | caggttacaa | cggccgtcct | cgttctcctc | 660 |
| tacggccaag | atactcccca | cggtaacaga | aaaaactcga | accagaacaa | actcacaatt | 720 |
| cctgaagaag | aagaagtact | agtagttgaa | gaagacgaac | gttccagttt | cgtcgagatc | 780 |
| ctaatcggcg | gacttggaaa | ttacagagcg | tggatcttag | cgctgctcta | cggatactcg | 840 |
| tacggcgtcg | agctaacgac | ggacaacgtg | atcgccggat | atttctacga | gagatttgga | 900 |
| gtgaatctgg | aggcggcggg | gacgatcgcg | gcgagtttcg | ggatatcgaa | cattgcgtcg | 960 |
| cgaccggcgg | gagggatgat | atcggatgcg | ctggggaaga | gattcggtat | gagagggagg | 1020 |
| ctgtgggggc | tatggatcgt | gcaatcggtg | gctgggttgt | tgtgcgtgtt | actcggacga | 1080 |
| gtcaactcgc | tctggggatc | aatcctcgtc | atgtgggtct | tctctgtttt | cgttcaagct | 1140 |
| gcttctggcc | ttgtatttgg | cgtggtccct | tcgtctcca | cgcggttagt | ttaaagtcta | 1200 |
| ccaatccggt | ttttgctaat | aatttcggtt | tggttttaat | ttggttttgt | ttataatgac | 1260 |
| agatcgttag | gagtggtggc | gggaattacg | ggaagcggcg | gtacggttgg | tgcggtggtg | 1320 |
| acgcagtttc | tgttgtttc | cggtgatgat | gttcgaaaac | agagaagcat | ttcacttatg | 1380 |
| ggtttgatga | cttttgtgtt | tgctctttct | gttacatcaa | tttactttcc | acaatggggt | 1440 |
| ggaatgtgtt | gtgggccttc | gtcatcttcc | gaagaagaag | atatttctcg | gggactcctt | 1500 |
| gtagaagacg | aagatgaaga | aggtaaagtg | gttagtggta | gtctacgtcc | cgtttgttga | 1560 |

<210> SEQ ID NO 4
<211> LENGTH: 1482
<212> TYPE: DNA
<213> ORGANISM: Arabidopsis thaliana

<400> SEQUENCE: 4

| atggagccat | ctcaacgcaa | caccaaaccg | ccgtcgtttt | cagattccac | tatcccggtt | 60 |

```
gattccgatg gtcgagccac cgtcttccga ccattctctc tctcctcgcc acactcacga    120
gcctttcacc tagcttggct ctcactcttc tcatgcttct tctccacctt ctccatccct    180
cctctggtcc ccgtcatctc ctccgacctc aacctctctg cctccaccgt atccgccgcc    240
ggaatcgctt cctcgctgg ctccatcttc tctcgcctcg ctatgggacc actctgtgat     300
ctcatcggac cacgtacttc ctcagcgatt ctctctttc tcaccgctcc tgtaatcctc     360
tccgcctcac tcgtctcctc tccgacgtcc ttcatcctcg tccgtttctt cgtcggcttc    420
tcgctcgcta atttcgtagc caatcaatac tggatgtcct ccatgttctc cggtaacgtc    480
attggtctcg ctaacggtgt ctcagccggt tgggctaacg tcggcgccgg tatctctcag    540
ctccttatgc ctctcatata ctccaccata gccgaattcc ttccacgcgc cgtcgcctgg    600
cgcgtgtcct tcgtatttcc cgccattttt caggttacaa cggccgtcct cgttctcctc    660
tacggccaag atactcccca cggtaacaga aaaaactcga accagaacaa actcacaatt    720
cctgaagaag aagaagtact agtagttgaa gaagacgaac gttccagttt cgtcgagatc    780
ctaatcggcg gacttggaaa ttacagagcg tggatcttag cgctgctcta cggatactcg    840
tacgcgtcg agctaacgac ggacaacgtg atcgccggat atttctacga gagatttgga    900
gtgaatctgg aggcggcggg gacgatcgcg gcgagtttcg ggatatcgaa cattgcgtcg    960
cgaccggcgg gagggatgat atcggatgcg ctggggaaga gattcggtat gagagggagg   1020
ctgtgggggc tatggatcgt gcaatcggtg gctgggttgt tgtgcgtgtt actcggacga   1080
gtcaactcgc tctggggatc aatcctcgtc atgtgggtct tctctgtttt cgttcaagct   1140
gcttctggcc ttgtatttgg cgtggtccct ttcgtctcca cgcggtcgtt aggagtggtg   1200
gcgggaatta cgggaagcgg cggtacggtt ggtgcggtgg tgacgcagtt tctgttgttt   1260
tccggtgatg atgttcgaaa acagagaagc atttcactta tgggtttgat gacttttgtg   1320
tttgctcttt ctgttacatc aatttactttt ccacaatggg gtggaatgtg ttgtgggcct   1380
tcgtcatctt ccgaagaaga agatatttct cggggactcc ttgtagaaga cgaagatgaa   1440
gaaggtaaag tggttagtgg tagtctacgt cccgtttgtt ga                      1482
```

<210> SEQ ID NO 5
<211> LENGTH: 493
<212> TYPE: PRT
<213> ORGANISM: Arabidopsis thaliana

<400> SEQUENCE: 5

Met Glu Pro Ser Gln Arg Asn Thr Lys Pro Pro Ser Phe Ser Asp Ser
1               5                   10                  15

Thr Ile Pro Val Asp Ser Asp Gly Arg Ala Thr Val Phe Arg Pro Phe
            20                  25                  30

Ser Leu Ser Ser Pro His Ser Arg Ala Phe His Leu Ala Trp Leu Ser
        35                  40                  45

Leu Phe Ser Cys Phe Phe Ser Thr Phe Ser Ile Pro Pro Leu Val Pro
    50                  55                  60

Val Ile Ser Ser Asp Leu Asn Leu Ser Ala Ser Thr Val Ser Ala Ala
65                  70                  75                  80

Gly Ile Ala Ser Phe Ala Gly Ser Ile Phe Ser Arg Leu Ala Met Gly
                85                  90                  95

Pro Leu Cys Asp Leu Ile Gly Pro Arg Thr Ser Ser Ala Ile Leu Ser
            100                 105                 110

Phe Leu Thr Ala Pro Val Ile Leu Ser Ala Ser Leu Val Ser Ser Pro

```
            115                 120                 125
Thr Ser Phe Ile Leu Val Arg Phe Phe Val Gly Phe Ser Leu Ala Asn
130                 135                 140

Phe Val Ala Asn Gln Tyr Trp Met Ser Ser Met Phe Ser Gly Asn Val
145                 150                 155                 160

Ile Gly Leu Ala Asn Gly Val Ser Ala Gly Trp Ala Asn Val Gly Ala
                165                 170                 175

Gly Ile Ser Gln Leu Leu Met Pro Leu Ile Tyr Ser Thr Ile Ala Glu
                180                 185                 190

Phe Leu Pro Arg Ala Val Ala Trp Arg Val Ser Phe Val Phe Pro Ala
                195                 200                 205

Ile Phe Gln Val Thr Thr Ala Val Leu Val Leu Leu Tyr Gly Gln Asp
210                 215                 220

Thr Pro His Gly Asn Arg Lys Asn Ser Asn Gln Asn Lys Leu Thr Ile
225                 230                 235                 240

Pro Glu Glu Glu Glu Val Leu Val Val Glu Glu Asp Glu Arg Ser Ser
                245                 250                 255

Phe Val Glu Ile Leu Ile Gly Gly Leu Gly Asn Tyr Arg Ala Trp Ile
                260                 265                 270

Leu Ala Leu Leu Tyr Gly Tyr Ser Tyr Gly Val Glu Leu Thr Thr Asp
                275                 280                 285

Asn Val Ile Ala Gly Tyr Phe Tyr Glu Arg Phe Gly Val Asn Leu Glu
                290                 295                 300

Ala Ala Gly Thr Ile Ala Ala Ser Phe Gly Ile Ser Asn Ile Ala Ser
305                 310                 315                 320

Arg Pro Ala Gly Gly Met Ile Ser Asp Ala Leu Gly Lys Arg Phe Gly
                325                 330                 335

Met Arg Gly Arg Leu Trp Gly Leu Trp Ile Val Gln Ser Val Ala Gly
                340                 345                 350

Leu Leu Cys Val Leu Leu Gly Arg Val Asn Ser Leu Trp Gly Ser Ile
                355                 360                 365

Leu Val Met Trp Val Phe Ser Val Phe Val Gln Ala Ala Ser Gly Leu
370                 375                 380

Val Phe Gly Val Val Pro Phe Val Ser Thr Arg Ser Leu Gly Val Val
385                 390                 395                 400

Ala Gly Ile Thr Gly Ser Gly Gly Thr Val Gly Ala Val Val Thr Gln
                405                 410                 415

Phe Leu Leu Phe Ser Gly Asp Asp Val Arg Lys Gln Arg Ser Ile Ser
                420                 425                 430

Leu Met Gly Leu Met Thr Phe Val Phe Ala Leu Ser Val Thr Ser Ile
                435                 440                 445

Tyr Phe Pro Gln Trp Gly Met Cys Cys Gly Pro Ser Ser Ser Ser
                450                 455                 460

Glu Glu Glu Asp Ile Ser Arg Gly Leu Leu Val Glu Asp Glu Asp
465                 470                 475                 480

Glu Gly Lys Val Val Ser Gly Ser Leu Arg Pro Val Cys
                485                 490

<210> SEQ ID NO 6
<211> LENGTH: 39
<212> TYPE: DNA
<213> ORGANISM: Arabidopsis thaliana

<400> SEQUENCE: 6
```

```
atcgagctcg gatccatgga gccatctcaa cgcaacacc                    39
```

<210> SEQ ID NO 7
<211> LENGTH: 36
<212> TYPE: DNA
<213> ORGANISM: Arabidopsis thaliana

<400> SEQUENCE: 7

```
atcgagctcg gtaccacaaa cgggacgtag actacc                       36
```

<210> SEQ ID NO 8
<211> LENGTH: 24
<212> TYPE: DNA
<213> ORGANISM: Arabidopsis thaliana

<400> SEQUENCE: 8

```
gcgccggtat ctctcagctc ctta                                    24
```

<210> SEQ ID NO 9
<211> LENGTH: 20
<212> TYPE: DNA
<213> ORGANISM: Arabidopsis thaliana

<400> SEQUENCE: 9

```
atatcatccc tcccgccggt                                         20
```

<210> SEQ ID NO 10
<211> LENGTH: 238
<212> TYPE: DNA
<213> ORGANISM: Cauliflower mosaic virus

<400> SEQUENCE: 10

```
agcttgtcaa catggtggag cacgacactc tcgtctactc caagaatatc aaagatacag      60
tctcagaaga ccagagggct attgagactt ttcaacaaag ggtaatatcg ggaaacctcc     120
tcggattcca ttgcccagct atctgtcact tcatcgaaag gacagtagaa aaggaagatg     180
gcttctacaa atgccatcat tgcgataaag gaaaggctat cgttcaagat gcctctac      238
```